(12) United States Patent
Gruber et al.

(10) Patent No.: US 6,706,512 B2
(45) Date of Patent: Mar. 16, 2004

(54) ANTITHROMBOTIC THROMBIN VARIANTS

(75) Inventors: Andras Gruber, Decatur, GA (US); Stephen R. Hanson, Stone Mountain, GA (US); Enrico De Cera, Ladue, MO (US)

(73) Assignee: Emory University, Atlanta, GA (US)

( * ) Notice: Subject to any disclaimer, the term of this patent is extended or adjusted under 35 U.S.C. 154(b) by 4 days.

(21) Appl. No.: 10/165,442

(22) Filed: Jun. 7, 2002

(65) Prior Publication Data

US 2003/0215440 A1 Nov. 20, 2003

Related U.S. Application Data

(60) Provisional application No. 60/297,089, filed on Jun. 8, 2001.

(51) Int. Cl.$^7$ .................. C12N 9/64; C12N 15/00; C12N 1/20; C07H 21/04
(52) U.S. Cl. ............. 435/226; 435/320.1; 435/325; 435/252.33; 435/23; 435/214; 536/23.2; 424/214
(58) Field of Search ................. 435/226, 320.1, 435/325, 252.33, 214, 23; 536/23.2; 424/214

(56) References Cited

PUBLICATIONS

Arosio, et al. —*Mutation of W215 Compromises Thrombin Cleavage of Fibrinogen, but Not of PAR–1 or Protein C*—Biochemistry 39, 8095–8101 (2000).
Bernard, et al. —*Efficacy and Safety of Recombinant Human Activated Protein C for Severe Sepsis*—N. Engl. J. Med. 344, 699–709 (2001).
Bonniec, et al. —*Glu–192→Gln substitution in thrombin mimics the catalytic switch induced by thrombomodulin*—Proc. Natl. Acad. Sci. 88, 7371–7375 (1991).
Bouton, et al. —*Role of the thrombin insertion loop 144–155, Study of thrombin mutations W148G, K154E and a thrombin–based synthetic peptide*—Eur. J. Biochem. 229, 526–532 (1995).
Cantwell & Di Cera —*Rational Design of a Potent Anticoagulant Thrombin*—Journal of Biological Chemistry 275, 39827–39830 (2000).
Di Cera —*Anticoagulant Thrombins*—Trends in Cardiovascular Medicine 8, 340–350 (1998).
Gibbs, et al. —*Conversion of thrombin into an anticoagulant by protein engineering*—Nature 378, 413–416 (1995).
Gresele, et al. —*Activated Human Protein C Prevents Thrombin–induced Thromboembolism in Mice*—Journal for Clinical Investigation 101, 667–676 (1998).
Gruber, et al. —*The Thrombin Mutant W215A/E217A Shows Safe and Potent Anticoagulant and Antithrombotic Effects in Vivo*—Journal of Biological Chemistry 277, 27581–27584 (2002).

Gruber, et al. —*Direct Detection of Activated Protein C in Blood from Human Subjects*—Blood 79, 2340–2348 (1992).
Gruber, et al. —*Inhibition of Platelet–Dependent Thrombus Formation by Human Activated Protein C in a Primate Model*—Blood 73, 639–642 (1989).
Guinto, et al. —*Unexpected crucial role of residue 225 in serine proteases*—Proc. Natl. Acad. Sci. USA 96, 1852–1857 (1999).
Hanson, et al. —*Antithrombotic Effects of Thrombin–induced Activation of Endogenous Protein C in Primates*—Journal for Clinical Investigation 92, 2003–2012 (1993).
Harker, et al. —*Experimental Arterial Thrombosis in Nonhuman Primates*—Circulation 83, IV–41–IV–55 (1991).
Ishii, et al. —*Thrombomodulin is Present in Human Plasma and Urine*—Journal for Clinical Investigation 76, 2178–2181 (1985).
Kogan, et al. —*Protein C Activator from the Venom of Aagkistrodon blomhoffi ussuriensis Retards Thrombus Formation in the Arterio–Venous Shunt in Rats*—Thrombosis Research 70, 385–393 (1993).
Leung, et al. —*Dissociation of Thrombin's Substrate Interactions Using Site–Directed Mutagenesis*—Trends in Cardiovascular Medicine 10, 89–92 (2000).
Marder, et al. —*Plasmin Induces Local Thrombolysis without Causing Hermorrhage: A Comparison with Tissue Plasminogen Activator in the Rabbit*—Thrombosis Haemostasis 86, 739–745 (2001).
Martinoli, et al. —*Fast Functional Protein C Assay Using Protac, A Novel Protein C Activator*—Thrombosis Research 43, 253–264 (1986).
McBane, et al. —*Antithrombotic Action of Endogenous Porcine Protein C Activated with a Latent Porcine Thrombin Preparation*—Thrombosis Haemostasis 74, 879–885 (1995).
Richardson, et al. —*Enhancing protein C interaction with thrombin results in a clot–activated anticoagulant*—Nature 360, 261–264 (1992).

(List continued on next page.)

*Primary Examiner*—Rebecca E. Prouty
*Assistant Examiner*—Sheridan L. Swope
(74) *Attorney, Agent, or Firm*—Womble Carlyle Sandridge & Rice, PLLC

(57) ABSTRACT

The present invention relates to novel antithrombotic variants of thrombin or fragments thereof that are capable of proteolytically activating protein C, but which are substantially free of fibrinogen cleavage activity. The present invention further relates to variant polypeptidess that may be cleaved to yield active thrombin variants. The present invention also relates to methods of inhibiting thrombus formation in an animal or human subject by delivering an antithrombotic variant thrombin of the present invention to the blood of the subject. The present invention relates also to methods that use the novel variant thrombins for determining the level of protein C activation in a blood sample, or the thrombogenic potential of a patient.

14 Claims, 15 Drawing Sheets

OTHER PUBLICATIONS

Sheehan, et al. —*Mutagenesis of Thrombin Selectively Modulates Inhibition by Serpins Heparin Cofactor II and Antithrombin III*—The Journal of Biological Chemistry 268, 3639–3645 (1993.

Takahashi, et al. —*Soluble Thrombomodulin Purified from Human Urine Exhibits a Potent Anticoagulant Effect in Vitro and In Vivo*—Thrombosis Haemostasis 73, 805–811 (1995).

Taylor, et al. —*Protein C Prevents the Coagulopathic and Lethal Effects of Escherichia coli Infusion in the baboon*—Journal for Clinical Investigation 79, 918–925 (1987).

Tsiang, et al. —*Protein Engineering Thrombin for Optimal Specificity and Potency of Anticoagulant Activity in Vivo*—Biochemistry 35, 16449–16457 (1996).

Vindigni, et al. —*Release of Fibrinopeptides by the Slow and Fast Forms of Thrombin*13 Biochemistry 35, 4417–4426 (1996).

Wu, et al. —*Single amino acid substitutions dissociate fibrinogen–clotting and thrombomodulin–binding activities of human thrombin*—Proc. Natl. Acad. Sci. 88, 6775–6779 (1991).

SEQ ID NO: 1

```
Thr Phe Gly Ser Gly Glu Ala Asp Cys Gly Leu Arg Pro Leu Phe Glu.16a
Lys Lys Ser Leu Glu Asp Lys Thr Glu Arg Glu Leu Leu Glu Ser Tyr
Ile Asp Gly Arg   36a
Ile Val Glu Gly Ser Asp Ala Glu Ile Gly Met Ser Pro Trp Gln Val.16
Met Leu Phe Arg Lys Ser Pro Gln Glu Leu Leu Cys Gly Ala Ser Leu
Ile Ser Asp Arg Trp Val Leu Thr Ala Ala His Cys Leu Leu Tyr Pro.48
Pro Trp Asp Lys Asn Phe Thr Glu Asn Asp Leu Leu Val Arg Ile Gly
Lys His Ser Arg Thr Arg Tyr Glu Arg Asn Ile Glu Lys Ile Ser Met.80
Leu Glu Lys Ile Tyr Ile His Pro Arg Tyr Asn Trp Arg Glu Asn Leu
Asp Arg Asp Ile Ala Leu Met Lys Leu Lys Pro Val Ala Phe Ser.112
Asp Tyr Ile His Pro Val Cys Leu Pro Asp Arg Glu Thr Ala Ala Ser
Leu Leu Gln Ala Gly Tyr Lys Gly Arg Val Thr Gly Trp Gly Asn Leu.144
Lys Glu Thr Trp Thr Ala Asn Val Gly Lys Gly Gln Pro Ser Val Leu
Gln Val Val Asn Leu Pro Ile Val Glu Arg Pro Val Cys Lys Asp Ser.176
Thr Arg Ile Arg Ile Thr Asp Asn Met Phe Cys Ala Gly Tyr Lys Pro
Asp Glu Gly Lys Arg Gly Asp Ala Cys Glu Gly Asp Ser Gly Gly Pro.208
Phe Val Met Lys Ser Pro Phe Asn Asn Arg Trp Tyr Gln Met Gly Ile
Val Ser Ala Gly Glu Gly Cys Asp Arg Asp Gly Lys Tyr Gly Phe Tyr.240
Thr His Val Phe Arg Leu Lys Lys Trp Ile Gln Lys Val Ile Asp Gln
Phe Gly Glu..259
```

*Fig. 1*

SEQ ID NO: 2

```
Ile Val Glu Gly Ser Asp Ala Glu Ile Gly Met Ser Pro Trp Gln Val.16
Met Leu Phe Arg Lys Ser Pro Gln Glu Leu Leu Cys Gly Ala Ser Leu
Ile Ser Asp Arg Trp Val Leu Thr Ala Ala His Cys Leu Leu Tyr Pro.48
Pro Trp Asp Lys Asn Phe Thr Glu Asn Asp Leu Leu Val Arg Ile Gly
Lys His Ser Arg Thr Arg Tyr Glu Arg Asn Ile Glu Lys Ile Ser Met.80
Leu Glu Lys Ile Tyr Ile His Pro Arg Tyr Asn Trp Arg Glu Asn Leu
Asp Arg Asp Ile Ala Leu Met Lys Leu Lys Lys Pro Val Ala Phe Ser.112
Asp Tyr Ile His Pro Val Cys Leu Pro Asp Arg Glu Thr Ala Ala Ser
Leu Leu Gln Ala Gly Tyr Lys Gly Arg Val Thr Gly Trp Gly Asn Leu.144
Lys Glu Thr Trp Thr Ala Asn Val Gly Lys Gly Gln Pro Ser Val Leu
Gln Val Val Asn Leu Pro Ile Val Glu Arg Pro Val Cys Lys Asp Ser.176
Thr Arg Ile Arg Ile Thr Asp Asn Met Phe Cys Ala Gly Tyr Lys Pro
Asp Glu Gly Lys Arg Gly Asp Ala Cys Glu Gly Asp Ser Gly Gly Pro.208
Phe Val Met Lys Ser Pro Phe Asn Asn Arg Trp Tyr Gln Met Gly Ile
Val Ser Ala Gly Glu Gly Cys Asp Arg Asp Gly Lys Tyr Gly Phe Tyr.240
Thr His Val Phe Arg Leu Lys Lys Trp Ile Gln Lys Val Ile Asp Gln
Phe Gly Glu..259
```

*Fig. 2*

SEQ ID NO: 3

```
Thr Phe Gly Ser Gly Glu Ala Asp Cys Gly Leu Arg Pro Leu Phe Glu.16a
Lys Lys Ser Leu Glu Asp Lys Thr Glu Arg Glu Leu Leu Glu Ser Tyr
Ile Asp Gly Arg    36a
Ile Val Glu Gly Ser Asp Ala Glu Ile Gly Met Ser Pro Trp Gln Val.16
Met Leu Phe Arg Lys Ser Pro Gln Glu Leu Leu Cys Gly Ala Ser Leu
Ile Ser Asp Arg Trp Val Leu Thr Ala Ala His Cys Leu Leu Tyr Pro.48
Pro Trp Asp Lys Asn Phe Thr Glu Asn Asp Leu Leu Val Arg Ile Gly
Lys His Ser Arg Thr Arg Tyr Glu Arg Asn Ile Glu Lys Ile Ser Met.80
Leu Glu Lys Ile Tyr Ile His Pro Arg Tyr Asn Trp Arg Glu Asn Leu
Asp Arg Asp Ile Ala Leu Met Lys Leu Lys Lys Pro Val Ala Phe Ser.112
Asp Tyr Ile His Pro Val Cys Leu Pro Asp Arg Glu Thr Ala Ala Ser
Leu Leu Gln Ala Gly Tyr Lys Gly Arg Val Thr Gly Trp Gly Asn Leu.144
Lys Glu Thr Trp Thr Ala Asn Val Gly Lys Gly Gln Pro Ser Val Leu
Gln Val Val Asn Leu Pro Ile Val Glu Arg Pro Val Cys Lys Asp Ser.176
Thr Arg Ile Arg Ile Thr Asp Asn Met Phe Cys Ala Gly Tyr Lys Pro
Asp Glu Gly Lys Arg Gly Asp Ala Cys Glu Gly Asp Ser Gly Gly Pro.208
Phe Val Met Lys Ser Pro Phe Asn Asn Arg Trp Tyr Gln Met Gly Ile
Val Ser Ala Gly Ala Gly Cys Asp Arg Asp Gly Lys Tyr Gly Phe Tyr.240
Thr His Val Phe Arg Leu Lys Lys Trp Ile Gln Lys Val Ile Asp Gln
Phe Gly Glu..259
```

*Fig. 3*

SEQ ID NO: 4

```
Ile Val Glu Gly Ser Asp Ala Glu Ile Gly Met Ser Pro Trp Gln Val.16
Met Leu Phe Arg Lys Ser Pro Gln Glu Leu Leu Cys Gly Ala Ser Leu
Ile Ser Asp Arg Trp Val Leu Thr Ala Ala His Cys Leu Leu Tyr Pro.48
Pro Trp Asp Lys Asn Phe Thr Glu Asn Asp Leu Leu Val Arg Ile Gly
Lys His Ser Arg Thr Arg Tyr Glu Arg Asn Ile Glu Lys Ile Ser Met.80
Leu Glu Lys Ile Tyr Ile His Pro Arg Tyr Asn Trp Arg Glu Asn Leu
Asp Arg Asp Ile Ala Leu Met Lys Leu Lys Lys Pro Val Ala Phe Ser.112
Asp Tyr Ile His Pro Val Cys Leu Pro Asp Arg Glu Thr Ala Ala Ser
Leu Leu Gln Ala Gly Tyr Lys Gly Arg Val Thr Gly Trp Gly Asn Leu.144
Lys Glu Thr Trp Thr Ala Asn Val Gly Lys Gly Gln Pro Ser Val Leu
Gln Val Val Asn Leu Pro Ile Val Glu Arg Pro Val Cys Lys Asp Ser.176
Thr Arg Ile Arg Ile Thr Asp Asn Met Phe Cys Ala Gly Tyr Lys Pro
Asp Glu Gly Lys Arg Gly Asp Ala Cys Glu Gly Asp Ser Gly Gly Pro.208
Phe Val Met Lys Ser Pro Phe Asn Asn Arg Trp Tyr Gln Met Gly Ile
Val Ser Ala Gly Ala Gly Cys Asp Arg Asp Gly Lys Tyr Gly Phe Tyr.240
Thr His Val Phe Arg Leu Lys Lys Trp Ile Gln Lys Val Ile Asp Gln
Phe Gly Glu..259
```

*Fig. 4*

SEQ ID NO: 5

```
acctttggctcgggagaggcagactgtgggctgcgacctctgttcgagaagaagtcgctg
gaggacaaaaccgaaagagagctcctggaatcctacatcgacgggcgcattgtggagggc
tcggatgcagagatcggcatgtcaccttggcaggtgatgcttttccggaagagtccccag
gagctgctgtgtggggccagcctcatcagtgaccgctgggtcctcaccgccgcccactgc
ctcctgtacccgccctgggacaagaacttcaccgagaatgaccttctggtgcgcattggc
aagcactcccgcaccaggtacgagcgaaacattgaaaagatatccatgttggaaaagatc
tacatccaccccaggtacaactggcgggagaacctggaccgggacattgccctgatgaag
ctgaagaagcctgttgccttcagtgactacattcaccctgtgtgtctgcccgacagggag
acggcagccagcttgctccaggctggatacaaggggcgggtgacaggctggggcaacctg
aaggagacgtggacagccaacgttggtaaggggcagcccagtgtcctgcaggtggtgaac
ctgcccattgtggagcggccggtctgcaaggactccacccggatccgcatcactgacaac
atgttctgtgctggttacaagcctgatgaagggaaacgagggatgcctgtgaaggtgac
agtggggaccctttgtcatgaagagccccttaacaaccgctggtatcaaatgggcatc
gtctcagcgggtgcaggctgtgaccgggatgggaaatatggcttctacacatgtgttc
cgcctgaagaagtggatacagaaggtcattgatcagtttggagagtag
```

Fig. 5

SEQ ID NO: 6 attgtggagggctcggatgcagagatcggcatgtcaccttggcaggtgatgcttttccggaa
gagtccccaggagctgctgtgtggggccagcctcatcagtgaccgctgggtcctcaccgccg
cccactgcctcctgtacccgccctgggacaagaacttcaccgagaatgaccttctggtgcgc
attggcaagcactcccgcaccaggtacgagcgaaacattgaaaagatatccatgttggaaaa
gatctacatccaccccaggtacaactggcgggagaacctggaccgggacattgccctgatga
agctgaagaagcctgttgccttcagtgactacattcaccctgtgtgtctgcccgacagggag
acggcagccagcttgctccaggctggatacaaggggcgggtgacaggctggggcaacctgaa
ggagacgtggacagccaacgttggtaaggggcagcccagtgtcctgcaggtggtgaacctgc
ccattgtggagcggccggtctgcaaggactccacccggatccgcatcactgacaacatgttc
tgtgctggttacaagcctgatgaagggaaacgaggggatgcctgtgaaggtgacagtggggg
accctttgtcatgaagagccccttcaacaaccgctggtatcaaatgggcatcgtctcagcgg
gtgcaggctgtgaccgggatgggaaatatggcttctacacacatgtgttccgcctgaagaag
tggatacagaaggtcattgatcagtttggagagtag

*Fig. 14*

ANTITHROMBOTIC THROMBIN VARIANTS

The present application claims the benefit of priority from a provisional application filed Jun. 8, 2001 and having U.S. Ser. No. 60/297,089.

ACKNOWLEDGMENT OF FEDERAL RESEARCH SUPPORT

This invention was made, at least in part, with funding from the National Institutes of Health with grants HL 49413 and HL 58141. Accordingly, the United States Government has certain rights in this invention.

FIELD OF THE INVENTION

The present invention relates generally to variant prothrombins and thrombins capable of activating protein C and having substantially reduced fibrinogen cleavage activity. More specifically, the invention relates to antithrombotic variant prothrombins and thrombins that have substantially reduced procoagulant activity, and to methods of reducing thrombus formation by administering the antithrombotic variant prothrombins or thrombins to an animal or human.

BACKGROUND

Thrombosis is caused by fibrin and platelet deposits that occlude blood vessels in various organs. The role of thrombosis in morbidity and mortality has been documented in many diseases, including, among others, deep vein thrombosis, pulmonary thrombo-embolism, myocardial infarction, ischemic stroke, anthrax and meningococcal sepsis, and heparin-induced thrombocytopenia. Macrovascular thrombosis can be prevented or successfully treated with anticoagulants, antiplatelet agents, and/or profibrinolytic agents. The antithrombotic therapy for microvascular thrombosis, however, presents a greater medical challenge. Pharmacological use of activated protein C (APC), a naturally circulating anticoagulant enzyme (Gruber et al. Blood 79: 2340–2348 (1992)) has been shown to reduce the mortality of severe sepsis (Bernard et al. New Eng. J. Med. 344: 699–709 (2001)). Clinical use of APC is now medically justifiable. However, manufacturing of injectable dosage forms of natural or recombinant APC for therapeutic use is expensive, especially in view of the large doses, such as, for example, administering 0.024 mg/kg/hour of recombinant human APC for the several days required for effective treatment.

The activation of naturally occurring physiologic systems leading to the production of endogenous therapeutic proteins can be as efficacious and more economical than administering the directly acting agent itself For example, relatively inexpensive plasminogen activators, such as streptokinase, are valuable in the systemic treatment of thrombosis, while the directly acting enzyme, plasmin, is suitable for topical therapy only (Marder et al. Thromb. Haemost. 86: 739–745 (2001)). An affordable alternative modality is needed to make APC-therapy accessible to a broader patient population, including those who suffer from septic disseminated intravascular coagulation due to sepsis.

Low dose wild-type human thrombin (WT) is a relatively safe antithrombotic agent in baboons (Hanson et al. J. Clin. Invest. 92: 2003–2012 (1993)) that is capable of binding to thrombomodulin and generating endogenous APC. However, the low-grade fibrin formation and platelet activation that accompany the infusion of WT have potentially adverse side-effects. WT not complexed with thrombomodulin can cause potentially fatal disseminated intravascular coagulation (Gresele et al. J. Clin. Invest. 101: 667–676 (1998)). Thrombomodulin deficiency or poor microcirculation in a patient pose additional safety risks. The use of guanidinobenzoyl thrombin for protein C activation has addressed several of these problems of WT because acyl-thrombin yields active thrombin by delayed deacylation after binding to endothelial thrombomodulin (McBane et al. Thromb. Haemost. 74: 879–885 (1995)). Acyl-thrombin is effective with a wider safety margin than WT in a pig model of thrombosis. The acylation approach, however, reduces, but does not eliminate, the potentially disastrous consequences of an inadvertent overdose, when simultaneous deacylation of unbound acyl-thrombin would suddenly clot all circulating blood.

Activation of the circulating protein C pool by a suitable snake venom activator has also been shown to produce antithrombotic effects in an arterio-venous (AV) shunt model (Kogan et al. Thromb. Res. 70: 385–393 (1993)). There are several potential advantages to snake enzymes, such as high specificity, long half-life, and stability. Immunogenecity, however, does present a problem if used repeatedly. Also, these enzymes are not readily available. In search for newer, specific, and safe protein C activators, a number of thrombin mutations have been reported to compromise cleavage of fibrinogen more than the activation of protein C (Cantwell et al. J. Biol. Chem. 275:39827–39830 (2000); Wu et al. Proc. Natl. Acad. Sci. U.S.A. 88:6775–6779 (1991); Gibbs et al. Nature 378: 413–416 (1995); Arosie et al. Biochemistry 39: 8095–8101 (2000)).

What is still needed, however, is an antithrombotic thrombin with a substantially reduced procoagulant activity and a compromised platelet activation activity, but having an effective capability to activate protein C.

What is also needed, therefore, is a variant thrombin that is practically devoid of activity towards fibrinogen and the platelet receptor PAR-1, but retains a significant capability to activate protein C in the presence of thrombomodulin.

What is still further needed are methods of administering to a patient variant thrombins capable of activating protein C but not of inducing thrombus formation.

What are also needed are methods to determine the antithrombotic potential and the status of activated protein C in the blood of an animal or human that do not necessitate the use of expensive protein C activators or the use of a protein C activator capable of inducing thrombus formation.

SUMMARY OF THE INVENTION

Briefly described, the present invention relates to novel antithrombotic variants of thrombin capable of proteolytically activating protein C, but which are substantially free of fibrinogen cleavage activity. The present invention further relates to variant prothrombins that may be cleaved to yield active thrombin variants. The present invention also relates to methods of inhibiting thrombus formation in an animal or human subject by delivering an antithrombotic variant thrombin of the present invention to the blood of the subject. The present invention relates also to methods that use the novel variant thrombins for determining the level of protein C activation in a blood sample or the thrombogenic potential of a patient.

The present invention provides variant prothrombins and thrombins that have substantially reduced fibrinogen cleavage activity and retain protein C activation activity. Nucleic acid encoding the variant prothrombins or thrombins of the present invention may be inserted into an expression vector and expressed in eukaryotic host cells. The secreted, glycosylated polypeptides may then be cleaved to the active variant thrombins and purified. The variant prothrombins and thrombins of the present invention are useful for administering to a patient as antithrombotic agents lacking a potent thrombus formation capability.

One aspect of the present invention provides variant prothrombins and thrombins that have a tryptophan-alanine substitution at the W215 position of the wild-type thrombin. The single mutant variant thrombin W215A has a substantially reduced fibrinogen cleavage activity and, therefore, a significantly reduced capability of thrombus formation in vivo, or procoagulant activity if contacted with blood in vitro. The variant thrombin W215A retains much of the activity of protein C activation seen with wild-type thrombin, and has an increased relative specificity with respect to PAR-1 cleavage.

Another aspect of the present invention provides a double mutant variant prothrombin and thrombin, WE, that have alanine substitutions at the W215 and E217 positions. The variant thrombin WE of the present invention has a substantially reduced fibrinogen cleavage activity, and significantly reduced PAR-1 cleavage activity (and hence reduced platelet activation activity). The WE variant retains a significant level of protein C activation activity. This variant thrombin, WE (W215A/E217A), is particularly useful for activating protein C, without either significantly cleaving fibrinogen or activating the PAR-1 under in vitro or in vivo conditions. Variant thrombin WE of the present invention has a significantly reduced capability to induce thrombus formation when delivered to the blood of animal or human patient.

The W215A/E217A substitutions of the WE variant thrombin of the present invention reverses the relative specificity of thrombin towards fibrinogen and protein C. The W215A/E217A mutant is substantially inactive toward the substrates fibrinogen and PAR-1, and does not detectably clot fibrinogen or activate platelets in vivo. The WE variant thrombin recovers almost its full activity toward protein C upon binding to thrombomodulin. The WE variant thrombin of the present invention cleaves and activates protein C in the presence of thrombomodulin at a rate only 6-fold slower compared to wild-type thrombin.

The extremely low activity toward prothrombotic substrates, the insignificant rate of inhibition by antithrombin III and the robust rate of hydrolysis of the anticoagulant substrate protein C in the presence of thrombomodulin endow the WE variant thrombin of the present invention with all the required properties of a desired potent antithrombotic thrombin. The mutant is practically inactive toward natural substrates until it binds to thrombomodulin and therefore it can exert its antithrombotic role in the entire blood circulation, particularly in the heart, the brain and the microcirculatory bed.

The variant prothrombins and thrombins of the present invention are useful antithrombotic, agents suitable for administering to a patient to inhibit thrombus formation by the activation of protein C. The present invention contemplates, that the prothrombins may be administered to an animal or human to be cleaved in vivo to deliver the corresponding variant thrombin to the blood.

Analogous to the endogenous fibrinolytic pathway, the anticoagulant capacity of a pharmacologically inducible endogenous protein C pathway surpasses the level that is needed and safe for therapeutic use. The variant thrombin WE of the present invention is useful for inducing the endogenous APC by the administration of low doses of the variant thrombin WE. This induction can be more efficient than using high-doses of administered exogenous APC, on a dosage-weight basis.

It is contemplated that the variant thrombins of the present invention are useful for determining the protein C activity in an individual. An especially useful variant thrombin is the double mutant WE that is both easier and cheaper to produce than alternative protein C activators such as snake venom. The protein C activity of a blood sample can be determined by using a variant thrombin of the present invention as an activator. One stage and multiple stage tests are contemplated by the present invention. A citrated venous, arterial or capillary blood sample may be added to a variant thrombin of the present invention. Contact between the protein C in the blood sample and the variant thrombin leads to the generation of APC. The resultant APC activity of the solution phase admixture may then measured by standard procedures.

Another assay method contemplated by the present invention is to add the blood sample to the variant thrombin protein C activator, a thrombomodulin analog, and calcium ions, with or without an APC chromogenic substrate. The rate of coagulation or cleavage of the chromogenic substrate will correspond to the level of protein C activity in the sample.

The present invention further contemplates an assay to determine the endogenous antithrombotic potential of the protein C system of an individual following the pharmacological induction of circulating APC activity in the blood. An increase in blood APC levels will follow administration of an effective amount of a protein C activator variant thrombin of the present invention. This global test will reflect the combined function of most components of the protein C system, notably protein C and thrombomodulin, but not of protein S. The subject will receive an effective dose of a protein C activator variant thrombin tol induce a temporary increase in the concentration of circulating APC that can be measured in one or more blood samples taken from the subject. This test, especially when combined with a protein C activity test, permits an assessment of the antithrombotic potential of the protein C pathway of an individual.

The present invention also contemplates a method of preparing activated protein C free of procoagulant and platelet activating activity. A protein C sample such as, for example, a protein C isolated from a biological fluid, or a protein C produced by recombinant DNA technology, can be converted into APC by contact with the protein C activator variant thrombin WE. The process can be terminated by separation of the activator variant thrombin from the substrate protein C, or by quenching the activity of the variant thrombin with an inhibitor. The activation process is particularly useful for manufacture of improved APC preparations from protein C for therapeutic purposes. The use of a variant thrombin, such as WE of the present invention, as the protein C activator ensures that the activated protein C preparation will not induce coagulant activity if administered to a patient.

DETAILED DESCRIPTION OF THE FIGURES

FIG. 1 illustrates the amino acid sequence of the thrombin variant W215A (SEQ ID NO: 1). The substitution W215A is in bold.

FIG. 2 illustrates the amino acid sequence of the thrombin variant W215A B-chain (SEQ ID NO: 2).

FIG. 3 illustrates the amino acid sequence of the thrombin variant W215A/E217A (SEQ ID NO: 3). The amino acid substitutions W215A and E217A are in bold.

FIG. 4 illustrates the amino acid sequence of the thrombin variant W215A/E217A (WE) B-chain (SEQ ID NO: 4).

FIG. 5 illustrates the nucleic acid sequence SEQ ID NO: 5 encoding the prothrombin variant W215A/E217A (SEQ ID NO: 3).

Figure 7:
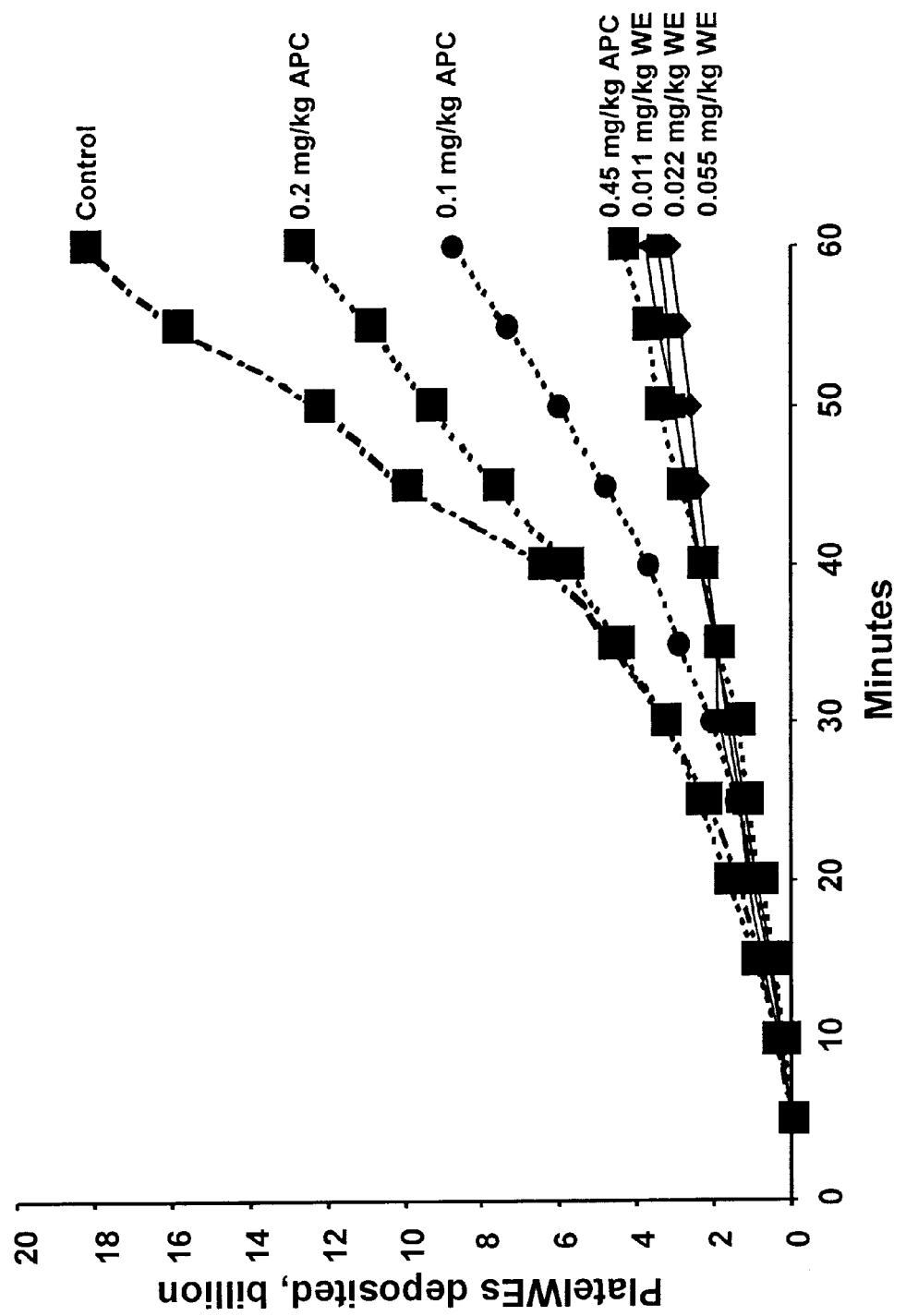

FIG. 7 illustrates antithrombotic platelet effects of APC and WE. Platelet deposition onto a thrombogenic device was measured by scintillation camera imaging during 60 mins. exposure arterial blood flow following insertion of the device into an AV shunt in baboons. Data were acquired and stored at 5 mins. intervals. Results are given as the averages of measurements from three different experiments for each 10 mins. data point, in control animals or following treatment with three different doses of APC or WE.

Figure 8:
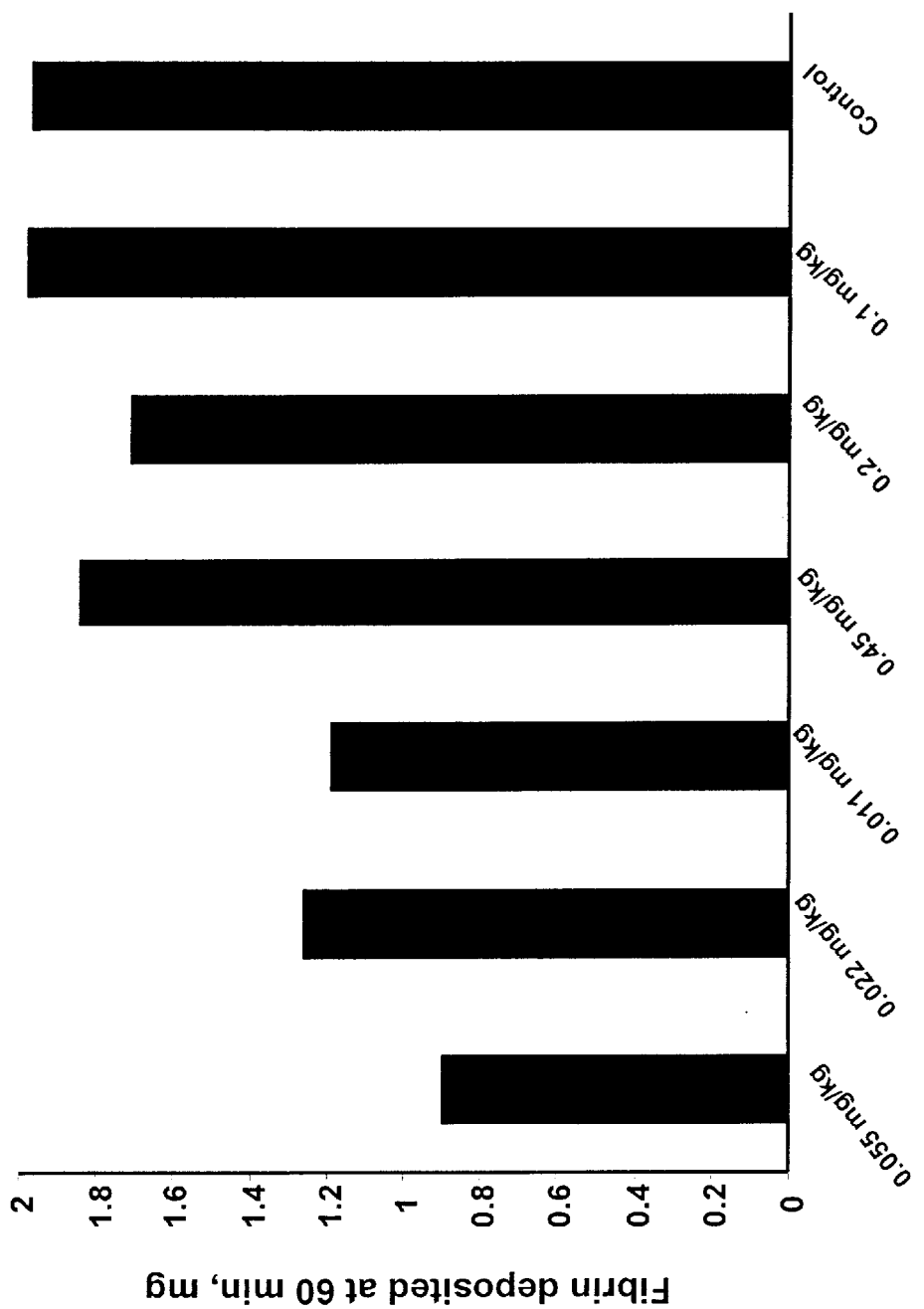

FIG. 8 illustrates the effects of APC and variant thrombin WE on fibrin thrombus deposition. The amount of fibrin deposited onto the Dacron graft segments after a 60 min. exposure to blood flow in control animals, and following treatment with three different doses of APC or WE. Results are given as the average of three experiments for each case. The antithrombotic effect of APC or WE treatment was assessed as the reduction in deposited fibrin vs. untreated controls.

Figure 9:
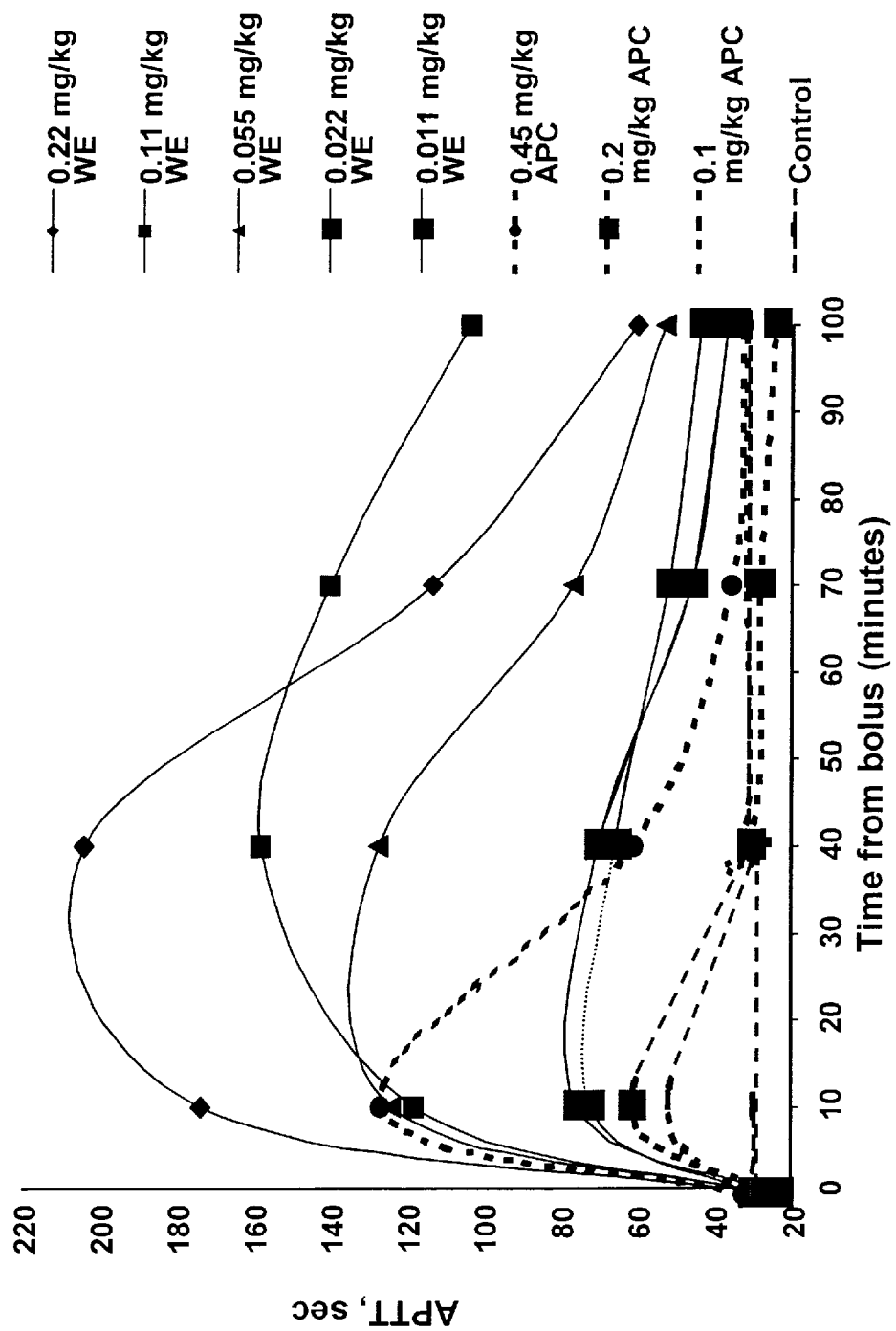

FIG. 9 illustrates the antihemostatic effects of APC and WE. APTT values in control animals, or following treatment with three different doses of APC or five different doses of WE. Each data point represents the average of three measurements from three separate experiments.

Figure 10:
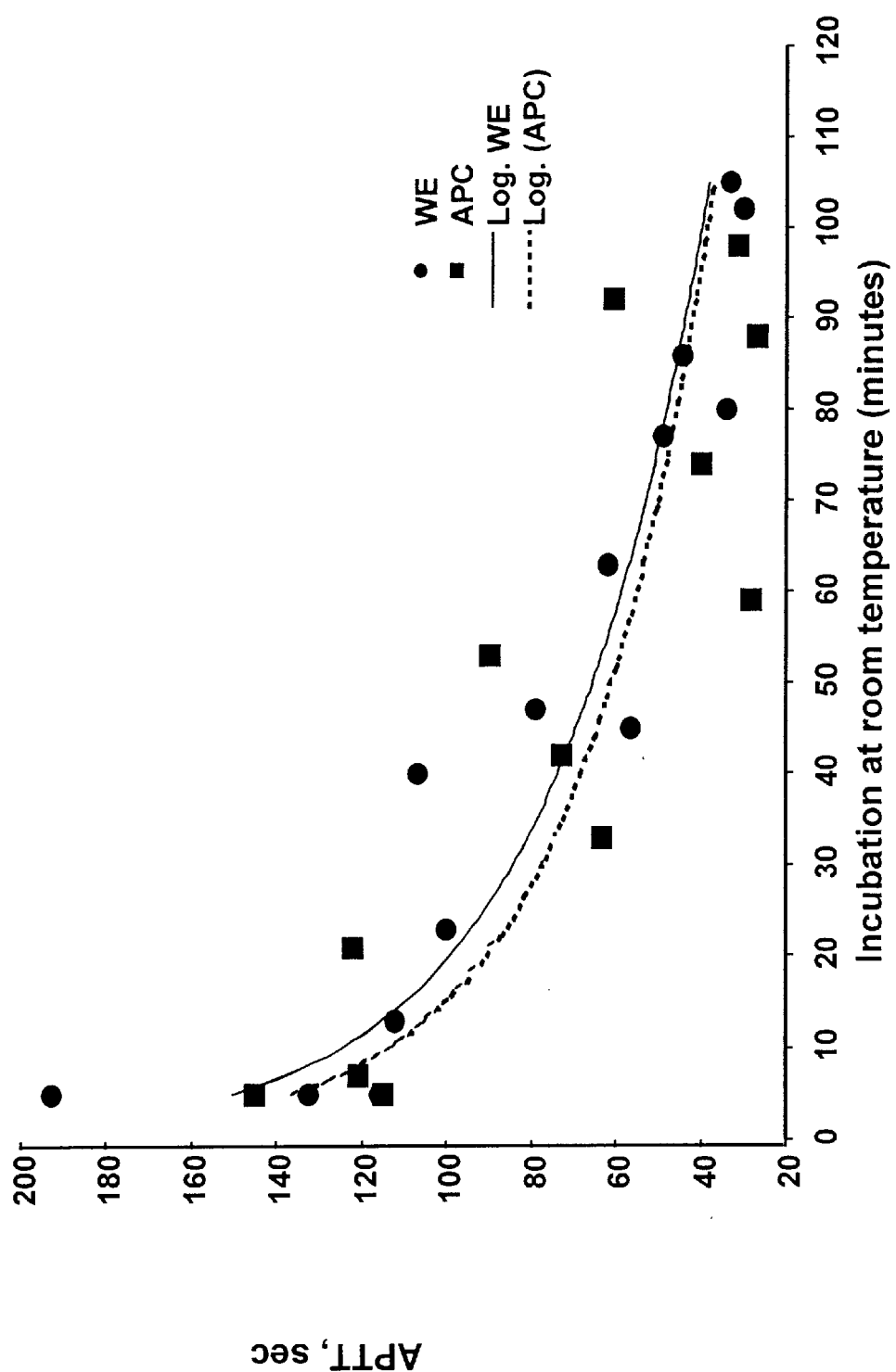

FIG. 10 illustrates the decay of the anticoagulant effects of exogenous or endogenous APC in plasma samples. When the APTT value was significantly prolonged, the test was repeated several times on the same sample for up to 100 mins. Because only APC is known to lose its anticoagulant activity within several hours in plasma, decreasing APTT values were considered indicative of APC in the circulation at the time of blood drawing. Citrated plasma samples with long APTT values, usually at 10 or 40 min. after dosing, were incubated at room temperature and the APTT test was repeated on 30 μl aliquots at random intervals. Results are shown for single measurements performed consecutively at least three times on all samples taken from animals treated with 0.45 mg/kg of APC (squares) or 0.055 mg/kg of variant thromnin WE (diamonds).

FIG. 11A illustrates the release of fibrinopeptides A (●) and B (○) by wild-type thrombin W215A.

FIG. 11B illustrates the release of fibrinopeptides A (●) and B (○) by variant thrombin W215A.

FIG. 11C illustrates the release of fibrinopeptides A (●) and B (○) by wild-type and variant thrombin WE (W215A/E217A).

Figure 12:
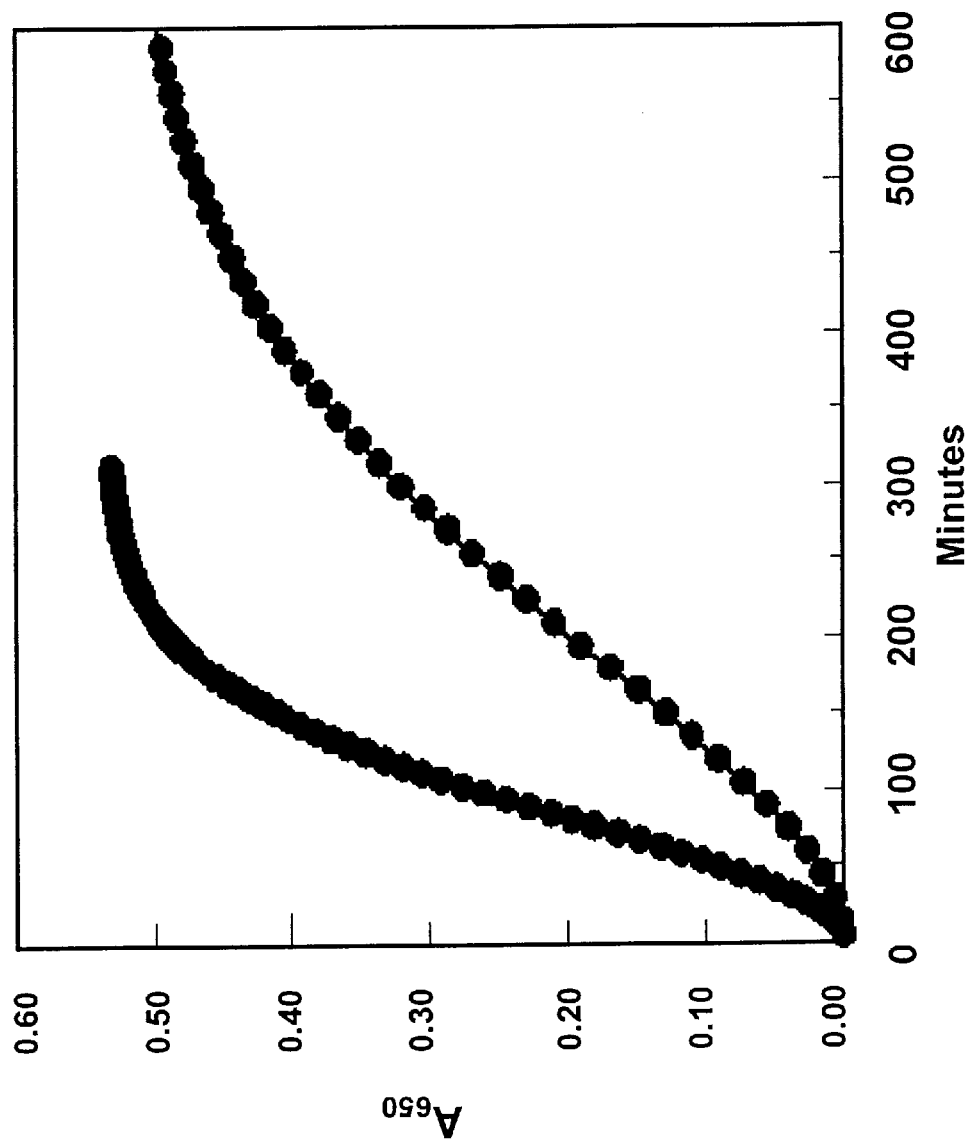

FIG. 12 illustrates the time-course for activation of protein C by wild-type thrombin (●) and the W215A/E126A mutant thrombin (○).

Figure 13A:
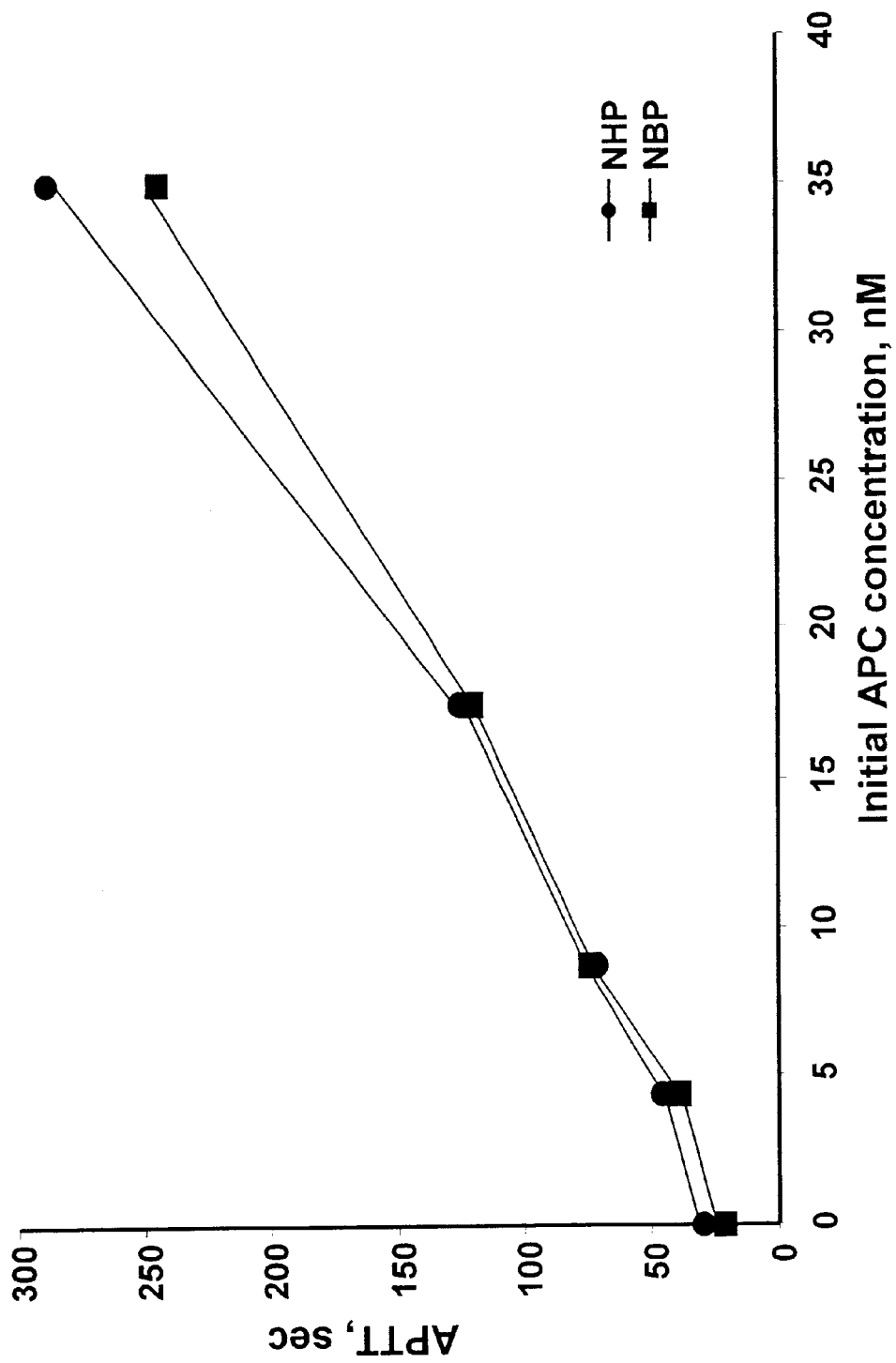

FIG. 13A illustrates the anticoagulant effect of APC in human and baboon plasma.

Figure 13B:
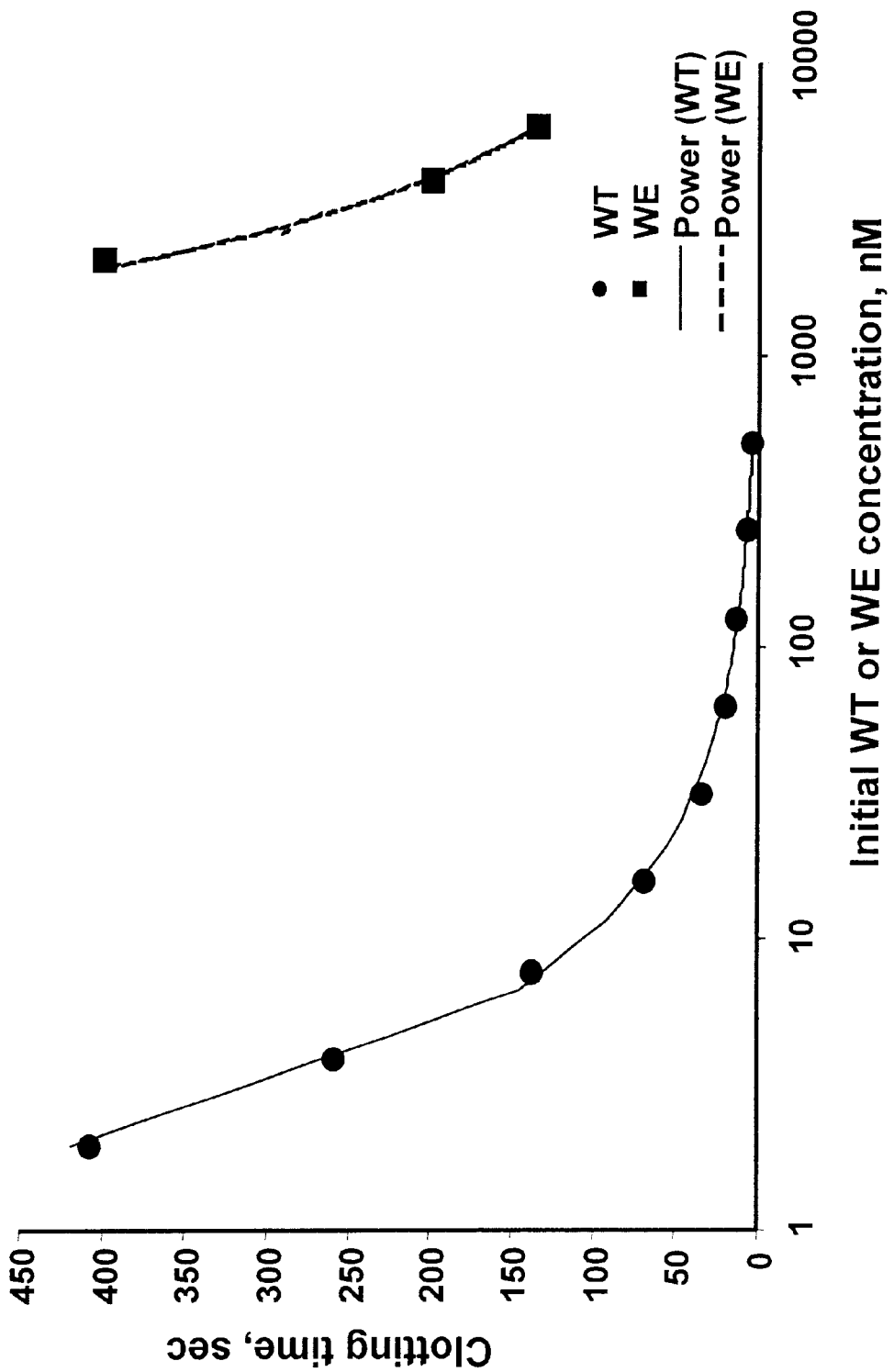

FIG. 13B illustrates the procoagulant effects of wild-type (WT) and the WE variant thrombin in baboon plasma.

FIG. 14 illustrates the nucleic acid sequence SEQ ID NO: 6 encoding the thrombin variant W215A/E217A (WE) B-chain (SEQ ID NO: 4).

DETAILED DESCRIPTION OF THE EMBODIMENTS OF THE INVENTION

Reference now will be made in detail to the presently preferred embodiments of the invention, one or more examples of which are illustrated in the accompanying drawings. Each example is provided by way of explanation of the invention, not limitation of the invention. In fact, it will be apparent to those skilled in the art that various modifications, combinations, additions, deletions and variations can be made in the present invention without departing from the scope or spirit of the invention. For instance, features illustrated or described as part of one embodiment can be used in another embodiment to yield a still further embodiment. It is intended that the present invention cover such modifications, combinations, additions, deletions and variations as fall within the scope of the appended claims and their equivalents.

Throughout this application various publications are referenced. The disclosures of these publications are hereby incorporated by reference in their entireties in this application to more fully describe the state of the art to which this invention pertains.

For convenience, certain terms employed in the specification, examples, and appended claims are collected here.

Definitions

The term "hemostasis" as used herein refers to a coordinated mechanism that maintains the integrity of blood circulation following injury to the vascular system. As used herein, "homeostasis" in the context of vascular physiology refers to the normal state of circulating blood that is maintained by feedback and regulation of the active components of the blood coagulation system. "Homeostasis" as used herein, therefore, is characterized by insignificant enzymic activity typically associated with blood coagulation or thrombus formation, such as, but not limited to, thrombin generation or platelet activation. In normal circulation without vascular injury, platelets are not activated and freely circulate. Vascular injury exposes sub-endothelial tissue to which platelets can adhere. Adherent platelets will attract other circulating platelets to form a preliminary plug that is particularly useful in closing a leak in a capillary or other small vessel. These events are termed primary hemostasis. This is, typically, rapidly followed by secondary hemostasis that involves a cascade of linked enzymic reactions that result in plasma coagulation to reinforce the primary platelet plug.

The term "coagulation" as used herein refers to the process of polymerization of fibrin monomers, resulting in the transformation of blood or plasma from a liquid to a gel phase. Coagulation of liquid blood may occur in vitro, intravascularly or at an exposed and injured tissue surface. In vitro blood coagulation results in a gelled blood that maintains the cellular and other blood components in essentially the same relative proportions as found in non-coagulated blood, except for a reduction in fibrinogen content and a corresponding increase in fibrin.

The term "thrombus" as used herein refers to a coagulated intravascular mass formed from the components of blood that results from a pathological condition of an animal or human. A thrombus comprises a cross-linked and concentrated mesh of fibrin monomers (fibrin polymer) that entrap platelets, and other blood cells. Typically the constituents of a thrombus have relative proportions differing from those of the same components in circulating blood. A thrombus is generated in vivo by a dynamic process that comprises cleavage of fibrinogen to fibrin, the activation of platelets and the adherence thereof to the cross-linked fibrin network. Integral to the process is the generation of thrombin from prothrombin by the combined intrinsic and extrinsic coagulation enzyme cascades. A thrombus may also serve to close an injured or severed blood vessel. The thrombus may also arise from injury to the endothelial cell layer lining the lumen of a blood vessel. The thrombus can then occlude the lumen of the vessel, reducing or preventing blood flow to an organ and possibly causing tissue damage or necrosis.

The term "thrombosis" as used herein refers to pathological formation of a blood clot, or thrombus, that results in restricted or blocked blood flow, with or without clinical symptoms. Thrombotic diseases include, but are not limited to, ischemic stroke, myocardial infraction, deep vein thrombosis, disseminated intravascular coagulation in sepsis and the like. The term "thromboembolism" as used herein refers to a blockage of a blood vessel due to the detachment of a thrombus from its site of origin and translocation to another site in the same or a different vessel.

The term "blood clot" as used herein refers to a viscous gel formed of, and containing all, components of blood in the same relative proportions as found in liquid blood. Thrombi are distinguished from blood clots as being formed under pathological conditions and having components in different relative proportions and interactions to those of liquid blood.

The term "hemorrhage" as used herein refers to clinically manifested internal or external bleeding following transvascular injury or a failure of hemostasis. Transvascular injury may be to any blood vessel, including, but not limited to, an artery, a vein, an arteriole, a venule or a capillary. Generalized perturbation of the hemostatic system, such as, for example, by the administration of an anticoagulant to a patient, may result in hemorrhage.

The term "thrombin" as used herein refers to a multifunctional prothrombin-derived enzyme. Thrombin acts as a procoagulant by the proteolytic cleavage of fibrinogen to fibrin. It also activates the clotting factors V, VIII, XI and XIII leading to perpetuation of clotting, and the cleavage of the platelet thrombin receptor PAR-1 leading to platelet activation. Multiple antithrombotic mechanisms limit thrombin generation and activity. When thrombin binds to thrombomodulin (TM), an integral membrane protein on vascular endothelial cells, thrombin undergoes a conformational change and loses its procoagulant activity. It then acquires the ability to convert protein C (PC) to activated protein C (APC). APC, a serine protease, acts as a potent anticoagulant by inactivating activated FV (FVa) and FVIII (FVIIIa), two essential cofactors in the clotting cascade. APC also inactivates plasminogen activator inhibitor-1 (PAI-1), the major physiologic inhibitor of tissue plasminogen activator (tPA), thus potentiating normal fibrinolysis.

Human thrombin is generated from a precursor polypeptide, prothrombin, of approximately 579 mature amino acids (subject to potential allelic variation or N-terminal microheterogeneity) plus a presequence of about 43 residues (Degen et al., Biochemistry 22:2087 (1993)). The presequence is proteolytically removed during expression and secretion of prothrombin.

Prothrombin is a zymogen, or inactive protease, that is activated by a series of proteolytic cleavages. At least three sites are subject to cleavage. In vivo, prothrombin is cleaved between residues R271 and T272 (Degen et al. residue numbers) by Factor Xa in the presence of Factor Va, phospholipid and calcium ions to yield prothrombin 2 and Fragment 1.2. Prothrombin is further proteolytically cleaved by the same system between residues R320 and I 321 to yield meizothrombin, which in turn cleaves autolytically between R155 and S156 to produce Fragment 1 (1–155) and meizothrombin des 1 (a disulfide linked dipeptide extending from residue 156 to the carboxy terminus of prothrombin, and cleaved at R323). Finally, thrombin is generated from prethrombin 2 by proteolytic cleavage between R320 and I321, or from meizothrombin des 1 by proteolytic cleavage between R271 and T272. Thrombin itself then autocleaves between T284 and T285 to generate the mature A-chain N-terminus.

Two distinct amino acid numbering systems are in use for thrombin in addition to the DNA-based system of Degen et al. (as used above). One is based on alignment with chymotrypsinogen as described in Bode et al. EMBO. J. 8:3467–3475 (1989), and used in this specification (except in FIGS. 1–4 where the Sadler system is used). In a second, the Sadler numbering scheme, the B chain of thrombin commences with I1 and extends to E259, while the A chain is designated with "a" postscripts as noted above, as in T1a to R36a. For example, Wu et al. in Proc. Natl. Acad. Sci. U.S.A. 88:6775–6779, (1991)) discloses several thrombin mutants numbered in accordance with the Sadler scheme. The Wu et al. mutants and the corresponding chymotrypsinogen and Degen et al. residue numbers, respectively, are sequentially shown as follows: H43 (57, 363), K52 (60f, 372), N53 (60g, 373), R62 (67, 382), R68 (73, 388), R70 (75, 390) D99 (102, 419) and S205 (195, 525). In this specification, therefore, W227 and E229, as designated by the Sadler system (as shown in FIGS. 1–4), are designated W215 and E217 respectively.

The terms "prothrombotic" and "prothrombotic agent" as used herein refer to an agent capable of inducing or accelerating pathological thrombus formation. Such factors include, but are not limited to, certain bacterial matter, activated coagulation factors, coagulation factor zymogens, thrombin having fibrinogen cleavage activity, and foreign matter.

The term "procoagulant" as used herein refers to agents that initiate or accelerate the process of blood coagulation through the transformation of soluble circulating fibrinogen to an insoluble cross-linked, fibrin network. In vitro, the procoagulant will ultimately yield a blood clot. In vivo, a procoagulant will ultimately yield a thrombus under pathological conditions. An exemplary procoagulant is native thrombin, or variants thereof, that has a proteolytic activity capable of cleaving fibrinogen to fibrin.

The term "anticoagulant" as used herein refers to any agent or agents capable of preventing or delaying blood clot formation in vitro and/or in vivo. Exemplary anticoagulants include chelating agents such as trisodium citrate and EDTA, oxalate and the like. Anticoagulants may also be indirect anticoagulants such as heparin, or direct anticoagulants such as, for example, melagatran. Such agents may be active only under in vitro conditions. For example, a chelating agent will prevent in vitro coagulation by removing free calcium ions from serum. In vivo, the removal of sufficient calcium ions to inhibit thrombus formation would require toxic levels of chelating agents. Natural anticoagulants that function in hemostasis to prevent systemic blood clotting include, but are not limited to, protein C, antithrombin III and thrombomodulin. Antithrombin III binds and inhibits thrombin and other factors of the coagulation enzyme cascades. Activated protein C is cleaved and activated by thrombin to activated protein C, which in turn, inactivates Factors Va and VIIIa of the coagulation cascade. Thus, thrombin also may induce in vivo anticoagulant activity due to the ability to activate protein C, as well as procoagulant activity due to the ability to cleave fibrinogen.

The term "antithrombotic" as used herein refers to agents that prevent the formation of, or destroy, a thrombus. Since a thrombus forms only under in vivo pathological conditions, an antithrombotic agent must be active in vivo, but not all antithrombotic agents are anticoagulants in vitro. Exemplary antithrombotic agents include, but are not limited to, aspirin, clopidogel, heparin and activated protein C that inhibit the formation of a thrombus, and streptokinase, urokinase, and plasmin that destroy a thrombus by cleavage of the cross-linked fibrin scaffold. Thrombin may have an antithrombotic activity by cleaving protein C to APC.

The term "coagulation cascade" as used herein refers to three interconnecting enzyme pathways as described, for example, by Manolin R in Wilson et al. (eds): Harrison's Principle of Internal Medicine, 14$^{th}$ Ed. New York. McGraw-Mill, 1998, p341, incorporated herein by reference in its entirety. The intrinsic coagulation pathway leads to the formation of Factor IXa, that in conjunction with Factors VIIIa and X, phospholipid and $Ca^{2+}$ gives Factor Xa. The extrinsic pathway gives Factor Xa and IXa after the combination of tissue factor and factor VII. The common coagulation pathway interacts with the blood coagulation Factors V, VIII, IX and X to cleave prothrombin to thrombin (Factor IIa), which is then able to cleave fibrinogen to fibrin.

As used herein the terms "polypeptide" and "protein" refer to a polymer of amino acids of three or more amino acids in a serial array, linked through peptide bonds. The term "polypeptide" includes proteins, protein fragments, protein analogues, oligopeptides and the like. The term "polypeptide" contemplates polypeptides as defined above that are encoded by nucleic acids, produced through recombinant technology, and isolated from an appropriate source such as a cell, cell culture fluid or a biological fluid from an animal or plant, or are synthesized. The term "polypeptide" further contemplates polypeptides as defined above that include chemically modified amino acids or amino acids covalently or noncovalently linked to labeling ligands.

The term "variant" as used herein refers to modified amino acid sequences derived from that of prothrombin, and which have amino acid substitutions at residue positions 215 and/or 217 of thrombin.

The term "PAR-1" as used herein refers to one member of the protease-activated receptor family of G-protein-coupled proteins. The PAR-1, which among other locations is found on the surface of platelets and endothelial cells, is specifically cleaved by thrombin to expose a tethered ligand capable of activating the receptor. The structure and biological functions of the PAR-1 (thrombin receptor) are described, for example, in Coughlin S. R. Thromb. Haemost. 86:298–307 (2001), incorporated herein by reference in the entirety.

The term "fibrinogen cleavage activity" as used herein refers to the ability of thrombin, or derivatives or variants thereof, to proteolytically cleave fibrinogen to give fibrin.

The term "PA/FC ratio" as used herein refers to the ratio of the percent of wild-type protein C activation (PA) activity remaining in a thrombin variant relative to the percent of wild-type fibrinogen clotting (FC) activity remaining in the thrombin variant. A value of PA/FC greater than 1.0 indicates that the thrombin variant has reduced procoagulant fibrinogen cleavage activity relative to the residual anticoagulant activity resulting from protein C activation.

The term "endothelial cell layer" as used herein refers to the inner cell layer lining the lumen of an artery, vein, arteriole, venule or to the constituent cells of vascular capillaries.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from the RNA nucleic acid molecule to yield a protein or polypeptide or a portion thereof The terms "nucleic acid vector" or "vector" as used herein refer to a natural or synthetic single or double stranded plasmid or viral nucleic acid molecule that can be transfected or transformed into cells and replicate independently of, or within, the host cell genome. A circular double stranded plasmid can be linearized by treatment with an appropriate restriction enzyme based on the nucleotide sequence of the plasmid vector. A nucleic acid can be inserted into a vector by cutting the vector with restriction enzymes and ligating the pieces together. The nucleic acid molecule can be RNA or DNA.

The term "plasmid" as used herein refers to a small, circular DNA vector capable of independent replication within a bacterial or yeast host cell.

The term "expression vector" as used herein refers to a nucleic acid vector that may further include at least one regulatory sequence operably linked to a nucleotide sequence coding for the desired polypeptide such as a variant thrombin of the present invention. Regulatory sequences are well recognized in the art and may be selected to ensure good expression of the linked nucleotide sequence without undue experimentation by those skilled in the art. As used herein, the term "regulatory sequences" includes promoters, enhancers, and other elements that may control expression. Standard molecular biology textbooks such as Sambrook et al. eds "Molecular Cloning: A Laboratory Manual" 2nd ed. Cold Spring Harbor Press (1989) and Lodish et al., eds., "Molecular Cell Biology," Freeman (2000) and incorporated herein by reference in their entireties, may be consulted to design suitable expression vectors, promoters, and other expression control elements. It should be recognized, however, that the choice of a suitable expression vector depends upon multiple factors including the choice of the host cell to be transformed and/or the type of protein to be expressed.

The term "recombinant cell" refers to a cell that has a new combination of nucleic acid segments that are not covalently linked to each other in nature. A new combination of nucleic acid segments can be introduced into an organism using a wide array of nucleic acid manipulation techniques available to those skilled in the art. A recombinant cell can be a single eukaryotic cell, or a single prokaryotic cell, or a mammalian cell. The recombinant cell can harbor a vector that is extragenomic. An extragenomic nucleic acid vector does not insert into the cell's genome. A recombinant cell can further harbor a vector or a portion thereof that is intragenomic.

The terms "percent sequence identity" or "percent sequence similarity" as used herein refer to the degree of sequence identity between two sequences as determined using the algorithm of Karlin & Atischul (1990) Proc. Natl. Acad. Sci. 87: 2264–2268, modified as in Karlin & Attschul (1 993) Proc. Natl. Acad. Sci. 90: 5873–5877. Such an algorithm is incorporated into the NBLAST and XBLAST programs of Attschul et al. (1990) T. Mol. Biol. Q15: 403–410. BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Attschul et al. (1997) Nuc. Acids Res. 25: 3389–3402. When utilizing BLAST and Gapped BLAST programs, the default parameters of the respective programs (e.g. XBLAST and NBLAST) are used. See http://www.ncbi.nlm.nih.gov.

Other algorithms, programs and default settings may also be suitable such as, but not only, the GCG-Sequence Analysis Package of the U.K. Human Genome Mapping Project Resource Centre that includes programs for nucleotide or amino acid sequence comparisons.

Pharmaceutical compositions comprising the variant thrombins of the present invention can be administered in dosages and by techniques well known to those skilled in the medical or veterinary arts, taking into consideration such factors as the age, sex, weight, species and condition of the particular patient, and the route of administration. The route of administration can be via any route that delivers a safe and effective dose of a composition of the present invention to the blood of an animal or human. Pharmaceutical or therapeutic compositions can be administered alone, or can be co-administered or sequentially administered with other treatments or therapies. Forms of administration, including injectable administration, include, but are not limited to, intravenous, intraperitoneal, an intramuscular, an intrathecal, an intraarticular, an intrapulmonary, an intraperitoneal, a retroperitoneal, an intrapleural, a subcutaneous, a percutaneous, a transmucosal, an oral, a gastro-intestinal, and an intraocular route of administration of such as sterile solutions, suspensions or emulsions. Pharmaceutical compositions may be administered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remmington's Pharmaceutical Science," 17th edition, 1985 may be consulted to prepare suitable preparations, without undue experimentation. The effective dosage and route of administration are determined by the therapeutic range and nature of the compound, and by known factors, such as the age, weight, and condition of the host, as well as $LD_{50}$ and other screening procedures that are known and do not require undue experimentation. Dosages can generally range from a few hundred micrograms to a few grams administered as a bolus or over a sustained period as determined by the medical condition and need of a subject animal or human. The term "sustained" as used herein refers to any extended period ranging from several minutes to years.

The term "pharmaceutically acceptable" as used herein refers to a compound or combination of compounds that while biologically active will not damage the physiology of the recipient human or animal to the extent that the viability of the recipient is comprised. Preferably, the administered compound or combination of compounds will elicit, at most, a temporary detrimental effect on the health of the recipient human or animal is reduced.

The term "intravascularly" as used herein refers to a route of delivering a fluid, such as a pharmaceutically acceptable composition, to a blood vessel.

The term "dosage" as used herein refers to the amount of a variant prothrombin or thrombin administered to an animal or human. Suitable dosage units for use in the methods of the present invention range from mg/kg body weight of the recipient subject to mg/kg. The therapeutic agent may be delivered to the recipient as a bolus or by a sustained (continuous or intermittent) delivery. When the delivery of a dosage is sustained over a period, which may be in the order of a few minutes to several days, weeks or months, or may be administer chronically for a period of years, the dosage may be expressed as weight of the therapeutic agent/kg body weight of the recipient/unit time of delivery.

The term "cardiovascular device" as used herein refers to a device or object operably connected to the vascular system of an animal or human and capable of receiving or channeling the flow of blood of an animal or human. The cardiovascular device may be external to the body of the animal or internal and includes, but is not limited to, group consisting of a stent, a vascular graft, an arterio-venous shunt, a cardiopulmonary bypass device, a cardiac assist device, a hemodialyzer and an artificial organ Abbreviations APC, activated protein C; WT, wild-type (thrombin); AV, arterio-venous; PPACK, H-D-Phe-Pro-ArgCH$_2$Cl; WE, variant thrombin having W215A/E217A substitutions; RAP, relative anticoagulant potency; LDPR, H-L-Leu-Asp-Pro-Arg-p-nitroanilide; PAR-1, protease activated receptor-1; FPR, H-D-Phe-Pro-Arg-p-nitroanilide.

The present invention provides variant prothrombins and thrombins useful as antithrombotic agents that have substantially reduced fibrinogen cleavage activity and retain protein C activation activity. It should be understood, however, that it is within the scope of the present invention for the active thrombin to comprise the thrombin B-chain, with or without covalently or non-covalently attached other polypeptides such as a thrombin A-chain.

The variant prothrombins and thrombins of the present invention are useful for administering to a patient as antithrombotic agents that lack a potent thrombus formation capability. The present invention further provides methods for administering the variant prothrombins and thrombins to the blood of an animal or human to inhibit the formation of a thrombus. The present invention also provides methods for using the variant thrombins to determine the protein C activity in an individual, the antithrombotic potential of the blood of an animal or human, and a method for producing activated protein C substantially free of undesired fibrinolytic cleavage activity.

It is to be understood that the present invention provides prothrombins and thrombins intended to include any of the following: mature human thrombin B chain (free of the A chain), human prothrombin containing both A and B chain, a fusion of a bacterial polypeptide with the human B chain thrombin, any fragment of the human thrombin B chain, so long as each of these derivatives retains the capability of activating protein C and has at least the amino acid substitution W215A and optionally the substitution E2167A, or can be processed to do so. Fragments of thrombin A or B chains, in particular of the B chain are included as well, again provided that the polypeptide in its entirety at least is capable of activating protein C. Fragments of thrombin may range from about 10, 20, 30, 50, 100 or more residues. Generally, polypeptides that contain more than one substitution in the thrombin sequence also will include the intervening thrombin sequence.

The present invention provides a prothrombin and a thrombin that have a tryptophan-alanine substitution at the W215 position of the wild-type thrombin (numbering relative to chymotrypsinogen). The W215A substitution was introduced into the wild type prothrombin amino acid sequence using PCR-based mutagenesis as described in Example 1, below. A nucleic acid encoding the W215A variant prothrombin may be inserted into an expression vector and expressed in eukaryotic host cells, as described in Example 1, below.

The nucleic acids for expression of the variant thrombins of the present invention may encode a preprothrombin containing the desired mutation since this permits facile expression and processing by methods heretofore used with thrombin. In addition, known methods for the recombinant expression of "gla-domainless" prothrombin are readily adapted to the preparation of the variant thrombins of this invention. It is within the scope of this invention to express a nucleic acid that encodes analogues of any of (a) prethrombin-2 (α-thrombin) or prethrombin-1, (b) the sequence of both chains of meizothrombin des 1 (which are either expressed as a single chain extending from S156 (Degan et al. Biochemistry 22: 2087 (1993)) to the 3' end of the nucleic acid encoding the B-chain, or are coexpressed as nucleic acids separately encoding the S156 fragment and the thrombin B chain), (c) thrombin (which is expressed as a single chain encoding both of the A and B chains, or is coexpressed in the same cell as nucleic acids separately encoding the A and B chains) or (d) the thrombin B chain free of the A chain. By "separately encoding" is meant that the A and B chain-encoding nucleic acids are separated by at least a stop codon and, if necessary, the downstream nucleic acid (usually B chain) commences with a start codon. Note, however, that bacterial polycistronic expression cassettes may require a unit such as an IRES, or may not require a start codon for the downstream coding sequence. Such heterodimeric expression systems generally are mammalian.

Polycistronic expression systems are useful for single cell coexpression of sequences comprising the two thrombin chains described above. These systems are known per se, and are particularly useful where, as here, it is desired to make the variant thrombin A and B chains of the present invention independently in the cell culture and thereby avoid any need for post-translational processing. In this instance both chains generally are expressed under the direction of the same expression control sequence (which chains and expression control sequences can be on the same or a different vector). However, the nucleic acid encoding each chain contains its own start codon as required and, preferably, each nucleic acid encodes its own signal sequence.

The variant thrombins of the present invention are optionally expressed as preproteins of α-thrombin or the A or B chains separately, whereby the variant thrombin is expressed as a precursor that is processed to the mature variant thrombin and secreted from the host cell. The presequences or signal sequences for use herein include the native presequence normally associated with the source of the thrombin gene, e.g. the human presequence for preprothrombin, or presequences that have amino acid sequences that are heterologous by sequence or origin to the prothrombin signal. Signal sequences optionally are derived from or are homologous to the host cell, or at least the phylogenetic branch to which the host cell belongs. For example, one ordinarily would use a presequence of a yeast protein, such as mating factor, in a yeast expression system, or of a bacterium, such as ST-II or beta-lactamase, in bacterial cell culture systems. It would be desirable to select signals from heterologous polypeptides that have mature N-terminal residue(s) that are the same as the mature thrombin A or B chains, and to use those signals with the N-terminally-homologous thrombin chain. A wide variety of suitable signal sequences are known and can be used in methods for the preparation of the NPs described herein.

The nucleic acid constructs encoding the secreted variant thrombins of the present invention generally will encode the thrombin A or B chains fused at their N-termini to the normal C-terminus of the same or different signal sequences. They are spliced into expression vectors under the control of expression control sequences such as promoters, operators, enhancers and polyadenylation sequences as is generally known in the art. Constructing suitable expression vectors for secreted or protoplasmically expressed NPs of this invention is a matter of routine for those skilled in the art, and will be accomplished using the conventional tools of molecular biology, including nucleic acid synthesis in vitro, PCR, adapters, ligases, restriction enzymes, expression and shuttle plasmids, transfection aids and the like, all of which are publicly (and for the most part commercially) available.

Suitable promoters or enhancers, termination sequences and other functionalities for use in the expression of NP in given recombinant host cells are well known, as are suitable host cells for transfection with nucleic acid encoding the desired variant thrombin. It may be optimal to use host cells that are capable of glycosylating the variant thrombins, which typically include mammalian cells such as embryonic kidney 293 cells, COS cells, CHO, BHK-21 cells and the like. In addition, host cells are suitable that have been used heretofore to express proteolytic enzymes or zymogens in recombinant cell culture, or which are known to already express high levels of such enzymes or zymogens in non-recombinant culture. In the latter case, if the endogenous enzyme or zymogen is difficult to separate from the variant thrombins then the endogenous gene should be removed by homologous recombination or its expression suppressed by cotransfecting the host cell with nucleic acid encoding an anti-sense sequence that is complementary to the RNA encoding the undesired polypeptide. In this case the expression control sequences (e.g., promoter, enhancers, etc.) used by the endogenous expressed gene optimally are used to control expression of the thrombin variants.

Host cells optimally will be selected that are devoid (in the relevant cell compartment) of proteolytic activity that is capable of intrachain cleavage of the thrombin A or B chains. Cells can be selected that contain no protease, e.g., in the periplasm, that will cleave after thrombin B R62, R123, R73, or K154, all of which are known to be sites of B chain degradation. For example, *E. coli* and other microbial strains are known that possess little or no extracellular or periplasmic proteolytic activity (other than signal peptidases). Such cells optimally would be used in expression systems in which the A and B chains are expressed in the same host cell fused to the same or different signal sequences. The A and B chains are co-secreted into the periplasm or extracellular medium where they become disulfide bonded. The absence of deleterious proteases helps to ensure that the product is not rendered microheterogenous as to chain length by host-endogenous proteases acting on the product NP, but of course independent A and B chain secretion is not dependent upon the use of such cells. In addition, or alternatively, the basic residues of the A or B chains that are sites for proteolytic cleavage are substituted with residues other than K or R.

The recombinant cells are cultured under conventional conditions and using conventional culture media heretofore employed with the cells in question. These conditions and media are widely known. Freshly transfected cells may only transiently express the variant thrombins, but stable transformants readily are obtained in accord with conventional practice using cotransformation with a selection gene such as DHFR or glutamine synthetase and serial culture in the presence of a selection agent such as methotrexate or methionine sulfoximine, respectively. It is desirable to screen for an expression system that will yield a quantity of thrombin that is at least about 75% of that obtained with the reference thrombin in the same expression system.

The variant thrombins of the present invention may be expressed as a properly assembled, disulfide bonded thrombin A and B chain analogue, or as the B chain analogue alone. In general, the polypeptide will be water soluble. It may be expressed in bacteria in the form of refractile bodies, in which case insoluble polypeptide is recovered and refolded using known methods, e.g. dissolution in guanidinium hydrochloride followed by gradual removal of the denaturant. Directly expressed variant thrombins of this invention may have an extra N-terminal methionine or blocked methionine residue, although host cells can be employed that will cleave away such extraneous N-terminal methionine residues.

If the A and B chains are fused together, for example, when expressed as the α-thrombin analogue, then post-translational proteolytic processing may be required in order to activate the precusor zymogen to the proteolytically active NP. Such precursors are analogous to naturally occurring prothrombins or may be fusions of one or both NP chains with a thrombin-heterologous polypeptide, as in the case of signal sequences. Proteolytic activation and/or processing is accomplished in the host cell culture itself, or can be done after recovery of the variant thrombin precursor (with or without intervening purification of the precursor). Post-translational proteolytic processing (either within the host cell culture or after initial recovery of the variant thrombin precursor) is used to remove any prothrombin (or prothrombin-heterologous) sequences that may be fused N-terminal to the A or B chain variant thrombins, or that is inserted elsewhere within a variant thrombin precursor.(e.g., antigen tags used to facilitate purification). The variant thrombin precursors are hydrolyzed by an enzyme or enzymes that is capable of making the correct cleavages without excessive or undesirable hydrolysis within the variant thrombin A or B chains. A generally suitable enzyme for removing pro sequence and activating native prothrombin is found in saw-scaled viper venom. Factor Xa also is useful to activate NP precursors. Proteolytic activation is not required by variant thrombin mature B chain or coexpressed individual mature A and B chains. Proteolytic activation can be accomplished at any point in the expression or purification of variant thrombin or its precursors, but typically is done after purification of variant thrombin precursors from the cells and/or cell culture supernatant.

It is also contemplated to be within the scope of the present invention, however, for the nucleic acid encoding variant prothrombins or thrombins to be expressed in a prokaryotic cell, whereupon the expressed polypeptide will not be post-translationally modified. The methods used for the cloning and expression are generally well known to those in the art, and described, for example in Sambrook et al. (1989) Molecular Cloning: A Laboratory Manual $_2^{nd}$ ed. Cold Spring Member Press, the content of which are incorporated herein in their entirety. The secreted, glycosylated thrombin may be cleaved to the active variant thrombin W215A and purified as described in Example 1 or may be produced as a prothrombin and subsequently cleaved as described above The amino acid sequence SEQ ID NO: 1 of the thrombin incorporating the W215A mutation of the present invention is shown in FIG. 1. The amino acid sequence SEQ ID NO: 2 of the W215A variant thrombin B-chain of the present invention is shown in FIG. 2.

The variant thrombin W215A of the present invention has a substantially reduced fibrinogen cleavage activity and, therefore, a significantly reduced capability of thrombus formation in vivo, or procoagulant activity if contacted with blood in vitro. Further, the variant thrombin W215A retains at least about 35% of the activity of protein C activation typically seen with wild-type thrombin, and has an increased relative specificity with respect to PAR-1 cleavage.

The W215A-containing variant thrombins of the present invention are useful antithrombotic agents for administering to a patient so as to inhibit thrombus formation by the activation of protein C, while concomitantly cleaving fibrinogen at a substantially reduced or negligible rate compared to what is obtained with wild-type (WT) thrombin. It is contemplated by the present invention that the prothrombin W215A may be delivered to the blood of an animal or human, whereupon it may be cleaved in vivo to deliver the corresponding thrombin W215A to the blood. The W215A substitution, as in the W215A variant prothrombin and thrombin of the present invention, is also particularly useful to be combined with a glutamate-alanine substitution at the E217 position of thrombin to generate a double mutant variant prothrombin or thrombin W215A/E217A (or WE) of the present invention.

Figure 6:
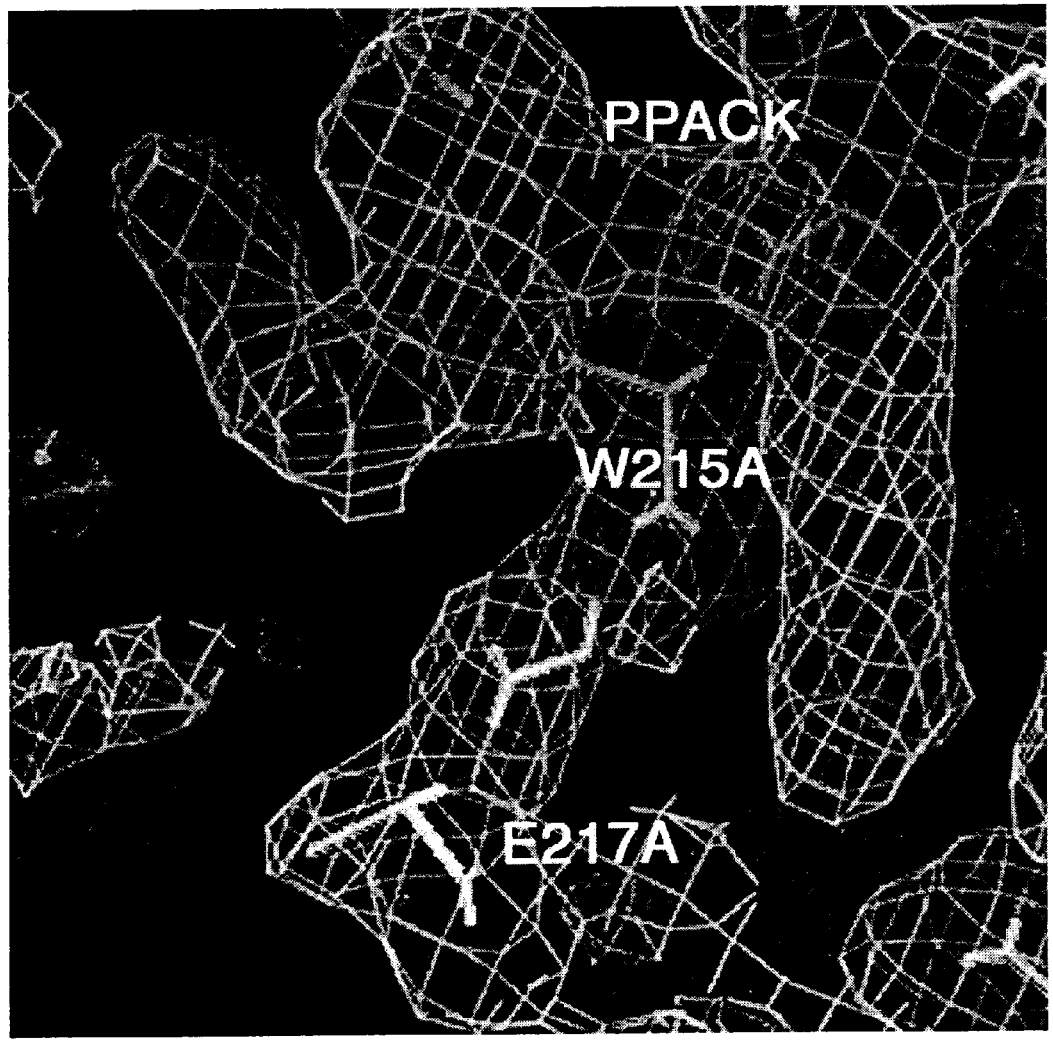
FIG. 6 illustrates the structure of the variant thrombin W215A/E217A (WE) around the PPACK binding site as determined from X-ray crystallographic data.

Another aspect, therefore, of the present invention provides a double mutant variant prothrombin or thrombin, WE, that has alanine substitutions both at the W215 and E217 positions. The amino acid sequence SEQ ID NO: 3 of the thrombin variant W215A/E217A is shown in FIG. 3, and that of the cleaved and enzymatically active thrombin variant WE B-chain (SEQ ID NO: 4) is given in FIG. 4. As with the W215A variant thrombin (SEQ ID NO: 1), the amino acid substitution were introduced into an isolated nucleic acid encoding the thrombin protein by PCR-based mutagenesis, as described in Example 1, below. The sequence of the thrombin-encoding nucleic acid (SEQ ID NO: 5) (GenBank Accessioin No. AY344793, having the W215A and E217A substitutions, is shown in FIG. 5. The sequence of the WE B-chain thrombin-encoding nucleic acid (SEQ ID NO: 12), having the W215A and E217A substitutions, is shown in FIG. 14. X-ray crystallographic data showing the orientation of the alanine substitutions in the double mutant W215A/E217A (WE) around the binding site of PPACK is shown in FIG. 6.

In contrast to the single substitution variant thrombin W215A of the present invention, variant thrombin WE of the present invention, while also having a substantially reduced fibrinogen cleavage activity, further has significantly reduced PAR-1 cleavage activity (hence reduced platelet activation activity). The WE variant, however, also retains a significant level of protein C activation activity, as shown in Examples 4 and 5. This aspect of the present invention, therefore, provides a unique variant thrombin, WE (W215A/E217A), that is particularly useful for activating protein C, without either significantly cleaving fibrinogen or activating the PAR-1 under in vitro or in vivo conditions. Variant thrombin WE of the present invention has a significantly reduced capability to induce thrombus formation when delivered to the blood of animal or human patient. Furthermore, by activating protein C, the variant WE thrombin exhibits anticoagulant properties, both in vivo and in vitro.

The value of $k_{cat}/K_m$ for the hydrolysis of H-D-Phe-Pro-Arg-p-nitroanilide drops over 25-fold in the E217A thrombin mutant disclosed by Gibbs et al. in U.S. Pat. Ser. No. 6,110,721. Cleavage of PAR-1 is compromised 40-fold. The effects of the E217A substitution had less effect on antithrombin III inhibition in the presence of heparin, and the cleavage of protein C in the absence of thrombomodulin. Thrombomodulin, however, almost completely eliminates any effect on protein C activation resulting from the E217A mutation. The value of $k_{cat}/K_m$ for the hydrolysis of protein C with thrombomodulin present is reduced only 30% relative to that of wild-type thrombin.

Compared to the wild-type (WT) thrombin activities, the W215A mutation of the present invention, as shown in Example 3 and Table 1, produces a significant loss (>100-fold) in $k_{cat}/K_m$ for the hydrolysis of fibrinogen, due entirely to an increase in $K_m$. The disruption of fibrinogen cleavage reaches 500-fold. By contrast, the reduction in antithrombin III binding and PAR-1 cleavage is about 20-fold. The activation of protein C is substantially reduced (150-fold) in the absence of thrombomodulin. Like the E217A mutation, the addition of thrombomodulin almost entirely eliminates the deleterious effects of the W215A mutation.

Both the E217A and W215A mutations of the WE variant thrombin of the present invention result in enhanced antithrombotic properties, as shown by the relative anticoagulant potency factor (RAP) shown in Table 2, below. This enhancement is the result of the pronounced deleterious effect of the mutations on fibrinogen cleavage, linked to only a modest decrease of protein C activation in the presence of thrombomodulin.

Variant Thrombin Having Single Mutation W215A

The W215A variant thrombin of the present invention releases fibrinopeptide A from fibrinogen and fibrinopetide B from fibrin with similar kinetics and rate constants. The Shafer mechanism of release of fibrinopeptides (Ng et al. Meth. Enzymol. 22: 341–358 (1993)) states that fibrinopeptide A is released first from fibrinogen leading to formation of fibrin I monomers. These monomers aggregate to form fibrin I protofibrils, from which fibrinopeptide B is released to give rise to fibrin II protofibrils that form the scaffold of a fibrin clot. Under conditions where thrombin concentration is rate-limiting, a lag phase occurs after the release of fibrinopeptide A before appreciable amounts of fibrinopeptide B are detected, as shown in FIG. 11. This mechanism is obeyed by wild-type thrombin WT (FIG. 11A), but does not hold for the W215A mutant (FIG. 11B). In this case, release of fibrinopeptide B occurs without delay (FIG. 11B) and with a rate constant slightly higher than that pertaining to fibrinopeptide A as shown in Example 3, Table 1.

The drastic perturbation of substrate binding seen in the case of fibrinogen by the variant thrombin W215A of the present invention is not matched by protein C activation in the presence of thrombomodulin. This substrate experiences only a modest loss of specificity, as the value of s drops 3-fold in the W215A mutant. The loss of specificity toward protein C is even less pronounced than that seen in the case of LDPR, a chromogenic substrate carrying Asp at P3 like protein C. The differential effect on the binding of fibrinogen and protein C makes the W215A variant thrombin of the present invention a particularly useful protein C activator. The gain in anticoagulant potency is larger than that of an E217K variant (Tsiang et al. Biochemistry 35: 16449–16457 (1996)).

The availability of a quantitative assay on the purified, extracellular fragment of PAR-1 enables the direct study of the structural components involved in PAR-1 binding (as discussed in Example 3). The kinetics of PAR-1 cleavage is first-order under the conditions tested and the $K_m$ is above 2 $\mu$M. This differs from previous data where the cleavage of PAR-1 was studied using a smaller fragment encompassing residues 38–60 of the thrombin receptor, that was found to be cut by thrombin with a higher value of s compared to $TR^{33-62}$ (Table 1) and a $K_m$=1.3 $\mu$M.

As a result of the replacement of tryptophan with alanine at position 215 in the variant thrombin W215A of the present invention, a differential effect on substrate recognition is seen. The W215A has severely compromised clotting activity (about a 500-fold reduction), with moderate loss of PAR-1 cleavage (26-fold reduction) and insignificant loss of protein C cleavage (only about 3-fold). Hence, the mutation of tryptophan 215 to alanine led to significantly different perturbations of the three important functions of thrombin, namely mediated by the cleavage of fibrinogen leading to clot formation, cleavage of PAR-1 leading to platelet aggregation, and cleavage of protein C leading to inactivation of Factor Va and reduced thrombin generation. Whereas a wild-type thrombin cleaves fibrinogen and PAR-1 with comparable specificity constants, the W215A mutant preferentially cleaves PAR-1, as shown in Table 1. Hence, the mutation of W215 to Ala affords a change of relative specificity of thrombin from fibrinogen to PAR-1.

The profile seen for PAR-1 cleavage in the variant thrombin W215A of the present invention is replicated by the interaction of antithrombin III in the presence of heparin (Table 1). The alanine substitution affords a decreased interaction of variant W215A with antithrombin III. The loss is only about 25-fold and compares well with PAR-1 cleavage.

W215 in thrombin interacts differently with different physiologic substrates. Mutation of W215 to Ala significantly compromises fibrinogen binding, to a lesser extent PAR-1 cleavage and has almost no effect on protein C cleavage in the presence of thrombomodulin. The molecular origin of this effect resides in the direct involvement of W215 in fibrinogen, but not protein C, recognition. A smaller secondary effect is generated by the loss of $Na^+$ binding in the W215A mutant and stabilization of the anticoagulant slow form of the enzyme.

The moderate effect on PAR-1 cleavage observed in the W215 substitution mutants is noteworthy. PAR-1 binds to the thrombin exosite I via a sequence that closely resembles the acidic C-tail of hirudin (Vu et al. Cell 64:1057–1068 (1991)). This interaction also mimics a similar interaction of the fibrinogen A$\alpha$ chain downstream to the site of cleavage by thrombin (Ni et al Biochemistry 28:3982–3094 (1989)). Perturbation of exosite I by enzymatic digestion with trypsin to produce $\gamma$-thrombin abrogates both fibrinogen and PAR-1 cleavage (Vu et al. Cell 64:1057–1068 (1991)). However, significant differences exist in the way fibrinogen and PAR-1 contact the active site of thrombin, with W215 making a direct interaction with fibrinogen but not PAR-1. Consequently, the W215A mutation produces a thrombin that cleaves PAR-1 with a specificity constant 20-fold higher than that of fibrinogen or protein C.

Variant Thrombins Having the Double Mutation W215A/E217A (WE)

The W215A/E217A substitutions of the WE variant thrombin of the present invention completely reverse the relative specificities of thrombin towards fibrinogen and protein C. Under physiologic conditions, wild-type thrombin cleaves fibrinogen with a $k_{cat}/K_m$ value about 80-fold higher than that relative to the cleavage of protein C in the presence of thrombomodulin. The W215A/E217A (WE) variant thrombin of the present invention cleaves protein C in the presence of thrombomodulin with a $k_{cat}/K_m$ value about 40-fold higher than that relative to the cleavage of fibrinogen. The change in specificity is further strengthened by a 3,000-fold reduction in the rate of inactivation by antithrombin III in the presence of heparin, as shown in Tables 2 and 3, below.

The W215A/E217A thrombin mutant is substantially inactive toward fibrinogen and PAR-1, and does not detectably clot fibrinogen or activate platelets in vivo. While 4 nM wild-type thrombin clots fibrinogen in about 30 secs, it may take 4 nM W215A/E217A mutant about a week to catalyze the same reaction. By contrast, the WE variant thrombin recovers almost its full activity toward protein C upon binding to thrombomodulin. The WE variant thrombin of the present invention cleaves and activate protein C in the presence of thrombomodulin at a rate only 6-fold slower compared to wild-type thrombin.

The extremely low activity toward prothrombotic substrates, the insignificant rate of inhibition by antithrombin III and the robust rate of hydrolysis of the anticoagulant substrate protein C in the presence of the physiologic cofactor thrombomodulin endow the WE variant thrombin of the present invention with all the desired properties of a potent antithromboti thrombin. The mutant is practically inactive toward natural substrates until it binds to thrombomodulin and therefore it can exert its antithrombotic role in the entire blood circulation, particularly in the heart, the brain and the microcirculatory bed.

The W215A/E217A (WE) thrombin double mutant has severely compromised amidolytic activity toward all substrates tested. Cleavage of H-D-Phe-Pro-Arg-p-nitroanilide is compromised over 30,000-fold, whereas cleavage of fibrinogen and fibrin are reduced 19,000-fold and 3,800-fold respectively, as shown in Table 1. The effects on fibrinogen and fibrin are additive ($\Delta G_c \approx 0$), whereas strong positive coupling in reducing specificity is present between the individual mutations in the hydrolysis of H-D-Phe-Pro-Arg-p-nitroanilide. The W215A/E217A double mutant releases the fibrinopeptides A and B with similar kinetics and rate constants as described in Example 9 below, and in FIGS. 11A–11C as seen for the W215A mutant (Arosio et al. Biochemistry 8095–8101 (2000)). This feature is not observed with the E217A mutant and therefore the structural origin of the effect can be assigned with certainty to the interaction of W215 with fibrinogen. Cleavage of PAR-1 by the W215A/E217A mutant is reduced 1,000-fold compared to wild-type and the effect of the individual mutations is additive, as seen for fibrinogen and fibrin recognition.

The remarkable feature of the W215A/E217A mutant is that activation of protein C is considerably less affected compared to the other substrates. The value of $k_{cat}/K_m$ is reduced 300-fold in the absence of thrombomodulin and only 7-fold in the presence of the cofactor, as described in Example 5 below. The presence of thrombomodulin alters the mechanism of recognition of protein C by thrombin, as demonstrated by the extraordinary increase (>1,000-fold) in specificity produced by binding of the cofactor.

In the case of thrombin, the coupling between mutations of W215 and E217 as assessed from the hydrolysis of H-D-Phe-Pro-Arg-p-nitroanilide does not coincide with that revealed by the interaction with fibrinogen or protein C in the presence of thrombomodulin, and is completely reversed in the case of the hydrolysis of protein C in the absence of cofactor.

The laboratory diagnosis of clinical thrombosis or disseminated intravascular coagulation is indicated by an acute decrease in fibrinogen and/or platelets in patients. All doses of a single bolus of the variant thrombin WE of the present invention actually prevented circulating fibrinogen and platelet consumption, notwithstanding the robust thrombogenic stimulus of a thrombogenic device in the subject monkey, as described in Examples 4 and 5, below. The variant thrombin WE of the present invention activates the endogenous protein C pathway and prevents clinically relevant procoagulant or prothrombotic effects. (platelet or fibrinogen consumption)

Most agents that exhibit antithrombotic effects, including APC, compromise coagulation- or platelet-dependent hemostasis to various degrees. Both APC and WE prolonged APTT. Since the clotting time of samples progressively decreased during incubation, the observed antithrombotic effect was due to the presence of circulating APC after injection of either APC or WE. The systemic anticoagulant response to all doses of the variant thrombin WE of the present invention lasted longer than the response to both exogenous APC, or the anticoagulant endogenous APC response to WT (Hanson et al. Clin. Invest. 92:2003–2012 (1993)).

The dynamics and time course of occlusive platelet-rich arterial-type thrombus formation in the standardized baboon model of acute platelet-dependent arterial thrombosis is likely to be similar to the events following the rupture of a coronary plaque (Harker et al. Circulation 83: 41–55 (1991)). A significant percentage of Dacron graft devices occlude without treatment within several hrs. Demonstrating efficacy on the Dacron graft comparable to that achieved by using WE usually requires relatively large and possibly unsafe doses of antithrombotic agents (Harker et al. Circulation 83: 41–55 (1991)) including high dose APC in this study. A near maximum effect and no dose response to WE suggests that the minimum efficacious dose of WE is less than about 0.011 mg/kg in the AV-shunt thrombosis model. The highest effective dose of APC appeared to be equiefficacious with the lowest dose of WE, since it potently inhibited platelet deposition but caused more APTT prolongation.

Bolus injections of WE or APC into subject animals allowed a comparison of the potencies of the two enzymes in an initially relatively stable biological system. Protein C activation may have occurred due to rapid formation of WE-thrombomodulin complexes on the endothelium, as described by Griffin in Nature 378: 337–338 (1995)), although soluble thrombomodulin (Ishii et al. J. Clin. Invest. 76: 2178–2181 (1985); Takahashi et al. Thromb. Haemost. 73: 805–811 (1995)) may also have played a role following injection of the WE variant. Whereas administration of APC had no effect on endogenous circulating plasma protein C activity, circulating protein C was consumed after injection of WE resulting in the partial protein C depletion within 100 mins. from dosing. A significant proportion of the circulating protein C can be converted into APC in the presence of the variant thrombin WE of the present invention that saturates endothelial and/or circulating thrombomodulin.

Analogous to the endogenous fibrinolytic pathway, the anticoagulant capacity of a pharmacologically inducible endogenous protein C pathway surpasses the level that is needed and safe for therapeutic use. The variant thrombin WE of the present invention is useful for inducing the endogenous APC by the administration of low doses of the variant thrombin WE. This induction can be more efficient than using high-doses of administered exogenous APC, on a dosage-weight basis.

Variant Thrombins WE and W215A as Diagnostic Tools and to Prepare Activated Protein C It is contemplated that the variant thrombins of the present invention are useful for determining the protein C activity in an individual. An especially useful variant thrombin is the double mutant WE that is both easier and cheaper to produce than alternative protein C activators such as snake venom.

The protein C activity of an anticoagulated or a native blood sample can be determined by using a variant thrombin of the present invention as an activator. One stage and multiple stage tests are contemplated by the present invention. In one embodiment of the present invention, therefore, a citrated venous, arterial or capillary blood sample may be collected, and an aliquot of the blood is added to a variant thrombin of the present invention. The protein C activator variant thrombin can be in a liquid or a dry form, wherein the protein can be, for example, in solution, lyophilized, or solid-phase bound such as to a gel matrix or other surface. Contact between the protein C in the blood sample and the variant thrombin leads to the generation of APC. The resultant APC activity of the solution phase admixture may then measured by standard procedures, such as by an appropriate clotting assay or a chromogenic assay, for example as described in Examples 8 and 11, below.

Another embodiment of the assay method contemplated by the present invention is to add the blood sample protein C activator to variant thrombin, a thrombomodulin analog, and calcium ions, with or without an APC chromogenic substrate. In this embodiment, the rate of coagulation or cleavage of the chromogenic substrate will correspond to the level of protein C activity in the sample. In yet another embodiment of the methods of the present invention, the protein C of the blood sample may be immobilized to a solid surface by such means as a linker anti-protein C-specific antibody that is attached to the solid surface. The immobilized protein C is contacted with fluid-phase protein C activator variant thrombin. The protein C activity may then be determined by comparing the APC activity of the test mixture to a known standard APC amount.

Native, non-anticoagulated, blood testing is most suitable for establishing the diagnosis of protein C deficiency at the point-of-care, i.e., rapidly in a surgical unit, for example, when immediate access to the data is required. Protein C activity tests of the present invention are further suitable to determine the status of the protein S system of an animal on human subject, as well as to measure the effect of detrimental mutations of coagulation factors, such as of Factor V and VIII. In this embodiment of the present invention, therefore, the assay may be performed in the presence and absence of added target factor, such as protein S, to be determined. The change in the level of activity of activated protein C will indicate the deficiency or otherwise of the target factor.

Another aspect of the present invention is an assay to determine the endogenous antithrombotic potential of the protein C system of an individual following the pharmacological induction of circulating APC activity in the blood of an animal or human subject. An increase in blood APC levels will follow administration of an effective amount of a protein C activator variant thrombin of the present invention. This global test will reflect the combined function of most components of the protein C system, notably protein C and thrombomodulin, but not of protein S. The subject, animal or human will receive an effective dose of a protein C activator variant thrombin WE, such as an intravenous bolus dose of 5 g/kg of WE in a pharmaceutically acceptable formulation. Such a dose of variant thrombin WE will induce a temporary increase in the concentration of circulating APC. The increase will occur within 10 minutes of administration and may last for several hours.

Circulating APC activity can be measured intone or more blood samples taken from the subject. Blood samples taken into citrate anticoagulant typically will be processed within 2 hours so that detectable APC remains in the sample. Blood samples taken into citrate and a reversible inhibitor of APC may be stored, frozen, and processed subsequently. The APC will be determined by coagulation tests or chromogenic detection methods such as described in Examples 8 and 11, below. Prior to testing, the sample may be diluted into a carrier or substrate solution, such as protein C deficient or factor V deficient plasma. The circulating level of APC then can be determined by comparing the results obtained with the test sample to known standards or results obtained from the reference population.

The amount of APC generated will show positive correlation with the concentration of protein C and thrombomodulin but negative correlation with inhibitors or antagonists of the protein C pathway. An inadequate APC response to administration of the protein C activator variant thrombin is diagnostic of a defect of the protein C system and of the antithrombotic potential of an individual. This test, especially when combined with a protein C activity test, permits an assessment of the antithrombotic potential of the protein C pathway of an individual.

Another aspect of the present invention is a method of preparing activated protein C free of procoagulant and platelet activating activity. A protein C sample such as, for example, a protein C isolated from a biological fluid, or a protein C produced by recombinant DNA technology, can be converted into APC by contact with a protein C activator variant thrombin for sufficient time to cleave most or all of the protein C in the preparation. The activator can be in fluid phase or attached to a solid phase medium, such as a gel matrix. At any desired degree of completion of the activation process, as determined by measuring APC activity in the preparation, the process can be terminated by separation of the activator variant thrombin from the substrate protein C, or by quenching the activity of the variant thrombin with an inhibitor. Suitable inhibitors include, for example, hirudin, hirudin analogs or small molecule direct thrombin inhibitors, such as melagatran. The activation process is particularly useful for manufacture of improved APC preparations from protein C for therapeutic purposes. Even after purification, the purified APC preparation might still have residual protein C activator levels. However, the use of a variant thrombin, such as WE of the present invention, as the protein C activator with substantially reduced fibrinogen cleavage activity ensures that the activated protein C preparation will not induce coagulant activity if administered to a patient.

One aspect of the present invention is a variant thrombin with reduced antithrombotic activity comprising an amino acid sequence having the amino acid substitutions W215A and E217A and at least 80% identical to the amino acid sequence set forth in SEQ ID NO: 3, wherein the variant thrombin has substantially reduced fibrinogen and PAR-1 receptor cleavage activity, and has protein C activation activity in the presence of thrombomodulin.

In one embodiment of the variant thrombins of the present invention, the variant thrombin comprises the B-chain having an amino acid sequence as set forth in SEQ ID NO: 4.

In another embodiment of the variant thrombins of the present invention, the variant thrombin having the W215A and E217A substitutions is encoded by a nucleic acid comprising a selected from SEQ ID NO: 5 and SEQ ID NO: 6 (GenBank Accession No. AY344794.

In yet another embodiment of the variant thrombins of the present invention, the variant thrombin having the W215A and E217A substitutions has a PA/FC ration greater than 1.0.

In still another embodiment of the variant thrombins of the present invention, the variant thrombin having the W215A and E217A substitutions has a PA/FC ration greater than 150.

In still yet another embodiment of the variant thrombins of the present invention, the variant thrombin having the W215A and E217A substitutions is expressed from a recombinant nucleic acid within a cell.

In one embodiment of the variant thrombins of the present invention, the variant thrombin having the W215A and E217A substitutions is encoded by a recombinant nucleic acid comprising the nucleic acid sequence as set forth in SEQ ID NO: 5, or a degenerate variant thereof.

In another embodiment of the variant thrombins of the present invention, the variant thrombin having the W215A and E217A substitutions is encoded by a recombinant nucleic acid in an expression cassette.

In yet another embodiment of the variant thrombins of the present invention, the expression cassette is in a vector.

Another embodiment of the present invention is a cell comprising a nucleic acid comprising the sequence as set forth in SEQ ID NO: 5, or a degenerate variant thereof, and capable of producing a variant thrombin protein at least 80% identical to the sequence set forth in SEQ ID NO: 3.

Another aspect of the present invention is a physiologically acceptable composition suitable for reducing thrombus formation in a recipient animal or human comprising a variant thrombin having protein C cleavage activity and a substantially reduced fibrinogen cleavage activity, and at least one pharmaceutically acceptable carrier.

In one embodiment of the physiologically acceptable composition of the present invention, the variant thrombin has the amino acid substitution W215A and is at least 80% identical to the amino acid sequence set forth in SEQ ID NO: 1.

In one embodiment of the physiologically acceptable composition of the present invention, the variant thrombin is a variant thrombin B-chain having the amino acid substitution W215A and comprising the amino acid sequence set forth in SEQ ID NO: 2.

In yet another embodiment of the physiologically acceptable composition of the present invention, the variant thrombin has the amino acid substitutions W215A and E217A and is at least 80% identical to the amino acid sequence set forth in SEQ ID NO: 3.

In still another embodiment of the physiologically acceptable composition of the present invention, the variant thrombin is a variant thrombin B-chain having the amino acid substitutions W215A and E217A and comprises the amino acid sequence set forth in SEQ ID NO: 4.

Another aspect of the present invention provides a method of inhibiting the formation of a thrombus, comprising the steps of delivering to the blood of an animal or human a physiologically acceptable composition comprising an effective amount of a variant thrombin with substantially reduced procoagulant activity, wherein the variant thrombin has the amino acid substitution W215A and comprises an amino acid sequence at least 80% identical to the amino acid sequence set forth in SEQ ID NO: 1, and allowing the variant thrombin to activate protein C, thereby inhibiting thrombus formation, but not substantially inducing fibrinogen cleavage activity.

In one embodiment of the method of the present invention, the variant thrombin has the amino acid sequence set forth in SEQ ID NO: 1.

In another embodiment of the method of the present invention, the variant thrombin is a variant thrombin B-chain comprises the amino acid sequence at least 80% identical to the amino acid sequence set forth in SEQ ID NO: 1.

In one embodiment of the method of the present invention, the variant thrombin B-chain comprises the amino acid sequence set forth in SEQ ID NO: 2.

In another embodiment of the method of the present invention, the variant thrombin further comprises the amino acid substitution E217A.

In one embodiment of the method of the present invention, the variant thrombin comprises the amino acid sequence at least 80% identical to the amino acid sequence set forth in SEQ ID NO: 3.

In another embodiment of the method of the present invention, the variant thrombin is a variant thrombin B-chain comprises the amino acid sequence at least 80% identical to set forth in SEQ ID NO: 4.

In still another embodiment of the method of the present invention, the variant thrombin comprises the amino acid sequence as set forth in SEQ ID NO: 3.

In one embodiment of the method of the present invention, the variant thrombin B-chain comprises the amino acid sequence set forth in SEQ ID NO: 4.

In still yet another embodiment of the method of the present invention, the variant thrombin further has a PA/FC ratio greater than 1.0.

In yet another embodiment of the method of the present invention, the variant thrombin further has a PA/FC ratio greater than 150.

In the various embodiments of the methods of the present invention, the physiologically acceptable composition further comprises a pharmaceutically acceptable carrier.

In the various embodiments of the methods of the present invention, the blood can be in a blood vessel selected from the group consisting of a heart, an artery, an arteriole, a venule, a vein, a fistula and a capillary.

In the various embodiments of the methods of the present invention, the blood can be in a device or vessel connecting to the vascular system device and selected from the group consisting of a stent, a cardiopulmonary assist or by-pass device, a hemodialysis device, a pump, an enteral or parenteral sustained-release device, a vascular graft, an arterio-shunt and an artificial organ.

Also, in various embodiments of the methods of the present invention, the effective amount of the variant thrombin is delivered to the lumen of a blood vessel of a recipient animal or human.

In various embodiments of the methods of the present invention, the effective amount of the variant thrombin is delivered to the blood as a bolus amount or over a sustained period.

In the various embodiments of the methods of the present invention, the effective amount of the variant thrombin can be delivered to the animal or human by an intravascular route.

In the various embodiments of the methods of the present invention, the effective amount of the variant thrombin is delivered to the animal or human by an intravascular infusion route selected from the group consisting of an intravascular injection, an intravascular drip and a catheter.

In the various embodiments of the methods of the present invention, the variant thrombin may be delivered to the blood of an animal or human by a route selected from the group consisting of a subcutaneous, intramuscular, intraperitoneal, intrapleural, intrathecal, intraarticular, epidural, enteral, percutaneous, transmucosal and intrapulmonary route.

In the various embodiments of the methods of the present invention, the effective amount of the variant thrombin may be administered at the dosage of between about 0.1 mg/kg/day to about 30 mg/kg/day.

Yet another aspect of the present invention is a method of inhibiting the formation of a thrombus, comprising the steps of delivering to the blood of an animal or human a physiologically acceptable composition comprising an effective amount of a variant thrombin with substantially reduced procoagulant activity, wherein the variant thrombin has the amino acid substitutions W215A and E217A and comprises an amino acid sequence at least 80% identical to the amino acid sequence set forth in SEQ ID NO: 3, and allowing the variant thrombin to activate protein C, thereby inhibiting thrombus formation.

In one embodiment of this aspect of the methods of the present invention, the variant thrombin is a variant thrombin B-chain comprising the amino acid sequence as set forth in SEQ ID NO: 4.

Another aspect of the present invention is a kit comprising a variant thrombin comprising an amino acid sequence selected from SEQ ID NOS: 1 and 3, and packaging comprising instructions for using the variant prothrombin to induce antithrombotic activity in a recipient animal or human.

In another embodiment of the kit of the present invention, the kit further comprises a pharmaceutically acceptable carrier and instructions for use in delivering the variant thrombin to an animal or human for use as an antithrombotic agent.

Yet another aspect of the present invention is a kit comprising a variant thrombin with reduced procoagulant activity and having the amino acid sequence set forth in SEQ ID NO: 1, and packaging comprising instructions for using the variant prothrombin to deliver thrombin as an antithrombotic agent in a recipient animal or human.

In one embodiment of the kit of the present invention, the kit further consists of a pharmaceutically acceptable carrier and instructions for use in delivering the variant thrombin to an animal or human.

Still yet another aspect of the present invention is a kit comprising a variant thrombin having the W215A and E217A substitutions with reduced prothrombotic activity and having the amino acid sequence set forth in SEQ ID NO: 3, and packaging comprising instructions for using the variant thrombin to induce antithrombotic activity in a recipient animal or human.

In another embodiment of the kit of the present invention, the kit further comprises a pharmaceutically acceptable carrier and instructions for use in delivering the variant thrombin to an animal or human.

Another aspect of the present invention is a method to determine the endogenous antithrombotic potential of the protein C system of an animal or patient, comprising the steps of administering to an animal or human an effective dose of a variant thrombin having a substantially reduced fibrinogen cleavage activity and capable of activating protein C, obtaining from the animal or human a blood sample, and measuring the coagulation rate or APC amidolytic activity thereof, and comparing the coagulation rate or APC amidolytic activity to the coagulation rate or APC amidolytic activity of a standard, thereby indicating the endogenous antithrombotic potential of the protein C system of the animal or human.

In one embodiment of this method, the variant thrombin comprises an amino acid sequence comprises an amino acid sequence at least 80% identical to an amino acid sequence selected from SEQ ID NOS: 1 and 3.

In one embodiment of this method, the variant thrombin comprises the amino acid sequence SEQ ID NO: 4.

Another aspect of the present invention provides kits comprising a variant thrombin with reduced prothrombotic activity and having the amino acid sequence selected from SEQ ID NO: 2 and 4, and packaging comprising instructions for using the variant thrombin B-chain to determine the protein C activity or the endogenous antithrombotic potential of the protein C system of an animal or human.

Another aspect of the present invention is a method to determine the endogenous antithrombotic potential of the protein C system of a patient, comprising the steps of administering to an animal or human an effective dose of a variant thrombin of the present invention having a substantially reduced fibrinogen cleavage activity and capable of activating protein C, obtaining a blood sample from the animal or human, measuring the coagulation rate or the APC amidolytic rate in the blood sample, comparing the coagulation rate or the APC amidolytic route to a standard and quantifying the protein C system of the animal or human.

Still yet another aspect of the present invention provides a method for producing activated protein C, comprising the steps of obtaining an sample of protein C, incubating the isolated protein C with a variant thrombin with reduced procoagulant activity, wherein the variant thrombin has the amino acid substitution W215A and an amino acid sequence at least 80% identical to the amino acid sequence set forth in SEQ ID NO: 1 and cleaving the isolated protein C by the variant thrombin, thereby yielding activated protein C.

In one embodiment of this method of the present invention, the variant thrombin has the amino acid sequence set forth in SEQ ID NO: 1.

In one embodiment of this method of the present invention, the variant thrombin further comprises the amino acid substitution E217A.

In another embodiment of this method of the present invention, the variant thrombin comprises an amino acid sequence at least 80% identical to the amino acid sequence as set forth in SEQ ID NO: 3.

In still another embodiment of this method of the present invention, the method further comprises the step of substantially purifying the activated protein C, wherein the purified activated protein C is substantially free from the variant thrombin and from fibrinogen cleavage activity.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the appended claims. In addition, it should be understood that aspects of the various embodiments may be interchanged both in whole or in part. The present invention is further illustrated by the following examples, which are provided by way of illustration and should not be construed as limiting. The contents of all references, published patents, and patents cited throughout the present application are also hereby incorporated by reference in their entireties.

EXAMPLE 1

Mutagenesis of Thrombin to Variants Having the W215A and W215A/E217A Substitution Site-directed mutagenesis of human α-thrombin was carried out in a HPC4-pNUT expression vector as described in Arosio et al. Biochemistry 39: 8095–8101 (2000) and incorporated herein by reference in its entirety, using overlap extension PCR with two mutant oligonucleotides: upstream: 5-GGGCATCGTCTCAXXXGGTGAAGGCTG TG-3 (SEQ ID NO: 7); downstream: 5-CACAGCCTT-CACCXXXTGAGACGATGCCC-3 (SEQ ID NO: 8) and two flanking oligonucleotide primers, BglII (upstream): 5-GAAGATCTACATCCACCCCAGG-3 (SEQ ID NO: 9 and; EcoRI (downstream): 5-TGACCATGATTACG-AATTC-3 (SEQ ID NO: 10). For the generation of the double mutant variant W215A/E217A (WE) thrombin, the forward primer 5'-GGGCATCGTCTCAGCGGGTGCA-GGCTGTGACCGGG-3' (SEQ ID NO: 11) and the reverse primer 5-CCCGGTCACAGCCTGCACCCGCTGAGAC-GATGCCC-3' (SEQ ID NO: 12) were used. Expression of the variant thrombins was carried out in baby hamster kidney cells as described in Guinto et al. Proc. Natl. Acad. Sci. U.S.A. 96: 1852–1857 (1999) incorporated herein by reference in its entirety. The enzyme was activated with the prothrombinase complex for about 30 mins. at 37° C. and then purified to homogeneity by monoS FPLC using a linear gradient of 0.05 to 0.5 M NaCl in 5 mM MES (pH 6) at room temperature. Mutants were further checked for incomplete refolding or autolytic digestion by N-terminal amino acid sequencing. Electrospray mass spectrometry yielded molecular weights consistent with the mutations introduced and indicated identical glycosylation in wild-type and mutant constructs. The active site concentration was determined by titration with hirudin and was found to be >90% in all cases.

EXAMPLE 2

Preparation and Safety of Antithrombotic Variant Thrombins

WT, W215A and WE variant thrombins were expressed, purified, and characterized in detail as described by Cantwell & Di Cera. J. Biol. Chem. 275: 39827–39830 (2000), incorporated herein by reference in its entirety. WE was stored in aliquots frozen until used in the thrombosis or coagulation experiments. To confirm that injection of variant thrombin WE would be at least as safe as injection of WT in baboons, the procoagulant activities of the two thrombins were compared in baboon plasma prepared by pooling citrated plasma samples from five animals. Citrated plasma was diluted 1:1 with isotonic saline, and the thrombin analogs were diluted with 0.1 M NaCl, 0.01 M $CaCl_2$, 0.02 M Tris, pH 7.3 prior to testing. 100 µl of thrombin analog was then added to 200 µl of baboon plasma and the clotting time was determined using a fibrometer. WE was at least 500-fold less procoagulant in baboon plasma than WT.

EXAMPLE 3

Assays for the Properties of Variant Thrombin W215A

All assays were carried out under experimental conditions of 5 mM Tris, 0.1% PEG, 145 mM NaCl, pH 7.4 at 37° C., unless otherwise specified. The chromogenic substrates FPR and LDPR were synthesized by solid phase, purified by HPLC and analyzed by mass spectrometry. Progress curves of the release of p-NA following the hydrolysis of chromogenic substrate were measured at 405 nm as a function of substrate concentration and analyzed to extract the values of $k_{cat}/K_m$ and $k_{cat}$, after proper correction for product inhibition. The activation of protein C in the presence of 100 nM rabbit thrombomodulin and 5 mM $CaCl_2$, the release of fibrinopeptide A from fibrinogen and fibrinopeptide B from fibrin, and the inhibition of thrombin by antithrombin III in the presence of 0.5 USP units/mL of heparin were carried out as described by Dang et al. in Nat. Biotechnol. 15: 146–149 (1997) and incorporated herein by reference in its entirety.

The interaction of the variant W215A thrombin with the platelet receptor PAR-1 was studied using the extracellular portion of the receptor spanning residues 33–62, $TR^{33-62}$. The fragment has an amino acid sequence A $^{33}$TNATLD-PRSFLLRNPNDKYEPFWEDEEKN$^{62}$ (SEQ ID NO: 13) and is cut by thrombin between R41 and S42 (Vu et al. Cell 64: 1057–1068 (1991)). $TR^{33-62}$ and its product of cleavage $TR^{33-41}$ have significantly different sizes and could be separated by reverse phase HPLC. Product formation and substrate depletion were monitored with a $C_{18}$ Waters Nova-pak column (4.6×250 mm, 4 µm). Optimal separation was obtained with a sodium phosphate buffer/acetonitrile linear gradient over 30 mins., at a flow rate of 1 mL/min. Extinction coefficients for $TR^{33-62}$ and its products of cleavage were derived by calibration and quantitative amino acid analysis of highly pure standards. Products were also analyzed by electrospray mass spectroscopy and N-terminal amino acid sequencing. The concentration of $TR^{33-62}$ was 2 µM, whereas enzyme concentrations ranged from 0.1 nM to 10 nM depending on the activity. Reactions were stopped at different times by addition of perchloric acid to a final concentration of 0.2 M. No degradation of $TR^{33-62}$ occurred in the absence of thrombin under all conditions tested. The concentration of the product $TR^{33-41}$ and the substrate $TR^{33-62}$ measured as a function of time was analyzed according to the kinetic equations $$[TR^{33-62}] = [TR^{33-62}]_0 \exp(-se_T t) \qquad (1)$$

$$[TR^{33-41}] = [TR^{33-41}]_\infty \{1 - \exp(-se_T t)\} \qquad (2)$$

where $s = k_{cat}/K_m$ is the specificity constant for the cleavage of $TR^{33-62}$ by thrombin and $e_T$ is the thrombin concentration. These equations are valid when the substrate concentration is below $K_m$. Attempts to measure the value of $K_m$ indicated a value >10 µM. The result of the assays of the activities of the variant W215A thrombin are given in Table 1 below.

TABLE 1

Specificity of wild-type and variant thrombin W215A.

|  | WT | W215A |
|---|---|---|
| $Na^+$ binding $K_d$ (mM)[a] | 66 ± 3 | 600 ± 200 |
| FPR[b] $k_{cat}/K_m$ (µM$^{-1}$s$^{-1}$) | 88 ± 4 | 0.91 ± 0.01 |
| $k_{cat}$ (s$^{-1}$) | 56 ± 3 | 43 ± 2 |
| LDPR[b,c] $k_{cat}/K_m$ (µM$^{-1}$s$^{-1}$) | 4.7 ± 0.9 | 0.025 ± 0.001 |
| Fibrinogen $k_{cat}/K_m$ (µM$^{-1}$s$^{-1}$)[d] | 17 ± 1 | 0.034 ± 0.002 |
| Fibrin $k_{cat}/K_m$ (µM$^{-1}$s$^{-1}$)[d] | 8.1 ± 0.5 | 0.053 ± 0.003 |
| Protein C $k_{cat}/K_m$ (µM$^{-1}$s$^{-1}$)[e] | 0.22 ± 0.01 | 0.075 ± 0.006 |
| PAR-1 $k_{cat}/K_m$ (µM$^{-1}$s$^{-1}$) | 26 ± 1 | 1.0 ± 0.1 |
| Antithrombin III $k_{on}$ (µM$^{-1}$s$^{-1}$)[f] | 13 ± 1 | 0.56 ± 0.04 |

Experimental conditions were 5 mM Tris, 0.1% PEG, 145 mM NaCl, pH 7.4, 37° C., unless otherwise noted.
[a]Derived from the linkage with hirudin binding under experimental conditions of 5 mM Tris, 0.1% PEG, pH 8.0, 25° C., I = 800 mM.
[b]Experimental conditions: of 5 mM Tris, 0.1% PEG, 200 mM NaCl, pH 8.0, 25° C.
[c]Values of $k_{cat}$ could not be estimated due to the very high $K_m$ of the substrate.
[d]Fibrinopeptide A released from fibrinogen and fibrinopeptide B released from fibrin I monomers.
[e]In the presence of 100 mM rabbit thrombomodulin and 5 mM $CaCl_2$.
[f]In the presence of 0.5 USP units/mL of heparin.

EXAMPLE 4

Assays for the Properties of Variant Thrombin W215A/E217A (WE) and Comparison With Variant Thrombin E217A All assays were carried out under experimental conditions of 5 mM Tris, 0.1% PEG, 145 mM NaCl, pH 7.4 at 37° C.

The chromogenic substrates H-D-Phe-Pro-Arg-p-nitroanilide specific for thrombin and H-D-Asp-Arg-Arg-p-nitroanilide specific for activated protein C were purchased from Midwest Bio-Tech (Carmel, Ind.). The values of $k_{cat}/K_m$ and $k_{cat}$ were obtained from the analysis of progress curves of the release of p-nitroaniline (measured at 405 nm) as a function of substrate concentration taking into account product inhibition, when present. The interaction of thrombin with fibrinogen and fibrin was studied in terms of the release of fibrinopeptides A and B as described by Vindigni & Di Cera. Biochemistry 35: 4417–4426 (1996) incorporated herein by reference in its entirety. The interaction of thrombin with PAR-1 was studied from the kinetics of cleavage of a soluble fragment corresponding to the extracellular portion of the receptor, as detailed in Arosio et al. Biochemistry 39: 8095–8101 (2000) incorporated herein by reference in its entirety. The inhibition of thrombin by antithrombin III in the presence of heparin, and the activation of protein C in the presence or absence of rabbit thrombomodulin were carried out and analyzed as described in Dang et al. Nat. Biotechnol. 15: 146–149 (1997).

The result of the assays of the activities of the variant W215A/E217A (WE) thrombin and a comparison with single mutant E217A variant thrombin are given in Table 2 below.

TABLE 2

Specificities of wild-type WT and variant thrombins E217A and W215A/E217 (WE).[a]

|  | WT | E217A | W215A/ E217A (WE) | $\Delta G_c$ |
|---|---|---|---|---|
| H-D-Phe-Pro-Arg-p-nitroanilide $k_{cat}/K_m$ ($\mu M^{-1}s^{-1}$) | 97 ± 5 | 3.8 ± 0.3 | 0.0028 ± 0.0001 | 1.6 ± 0.1 |
| Fibrinogen $k_{cat}/K_m$ ($\mu M^{-1}s^{-1}$) | 17 ± 1 | 0.27 ± 0.02 | 0.00089 ± 0.00007 | −0.3 ± 0.1 |
| Fibrin $k_{cat}/K_m$ ($\mu M^{-1}s^{-1}$) | 8.1 ± 0.5 | 0.15 ± 0.02 | 0.0021 ± 0.0001 | −0.5 ± 0.1 |
| Protein C − TM $k_{cat}/K_m$ ($M^{-1}s^{-1}$)[b] | 150 ± 10 | 15 ± 1 | 0.57 ± 0.03 | −1.1 ± 0.1 |
| Protein C + TM $k_{cat}/K_m$ ($mM^{-1}s^{-1}$)[c] | 220 ± 10 | 140 ± 10 | 33 ± 2 | 0.2 ± 0.1 |
| PAR1 $k_{cat}/K_m$ ($\mu M^{-1}s^{-1}$) | 26 ± 1 | 0.66 ± 0.01 | 0.026 ± 0.001 | 0.00 ± 0.1 |
| Antithrombin III $k_{on}$ ($\mu M^{-1}s^{-1}$)[d] | 13 ± 1 | 1.0 ± 0.1 | 0.0040 ± 0.0003 | 1.5 ± 0.1 |
| RAP[e] | 1 | 40 ± 3 | 2800 ± 300 | |

[a]Experimental conditions were 5 mM Tris, 0.1% PEG, 145 mM NaCl, pH 7.4, 37° C.
[b]In the absence of rabbit thrombomodulin, but in the presence of and 5 mM CaCl$_2$.
[c]In the presence of 100 nM rabbit thrombodulin and 5 mM CaCl$_2$.
[d]In the presence of 0.5 USP units/mL of heparin.
[e]Relative anticoagulant potency calculated as the ratio of the rate for protein C activation over the rate for fibrinopeptide A release, relative to the same ratio of wild-type thrombin (Di Cera, E., Trends Cardiovasc. Med. 8: 340–350 (1998)).
The value of $\Delta G_c$, in kcal/mol, was calculated using the values of $s = k_{cat}/K_m$ for wild-type and mutants given in the table.

EXAMPLE 5

Antithrombotic Platelet Effects of APC and WE

The antithrombotic effects of escalating doses of WE were compared to three doses of exogenous APC in baboons, using a thrombogenic AV shunt. Platelet count and fibrinogen levels moderately decreased during the 60-mins. shunt thrombosis in untreated controls but not in WE- or APC-treated animals, as shown in Table 3, below.

The number of platelets deposited on a thrombogenic device was determined twelve times consecutively during 60 mins. arterial blood flow through an AV shunt in baboons were investigated. The antithrombotic effects of both APC and WE were tested at three dose levels in three awake juvenile baboons. Intravenous bolus injections of 0.1, 0.2 or 0.45 mg/kg (1.8, 3.6 or 8 nmoles/kg) of APC, or 0.011, 0.022, or 0.055 mg/kg (0.3, 0.6, or 1.5 nmoles/kg) of WE in 10 mL sterile solution containing 2.5% dextrose and 0.45% saline were given to each study subject at time 0 (initial body weight range 9.35 to 10.75 kg). The theoretical peak concentrations of the enzymes in circulating blood were in the range of 30 to 80 nM (1.7 to 7.5 μg/mL) for APC and 1.95 to 40 nM (0.18 to 3.67 μg/mL) for WE. Ten minutes after the WE or APC bolus, a thrombogenic device was inserted into chronic exteriorized AV shunts, and the deposition of radiolabeled platelets on the device was monitored for one hour, essentially as described by Hanson et al. In J. Clin. Invest.; 92: 2003–2012(1993) incorporated herein by reference in its entirety, with minor modifications as follows. The thrombogenic device was a 120 cm long, 3 mm internal diameter silicon rubber shunt containing a highly thrombogenic 2 cm long 4 mm internal diameter knitted Dacron vascular graft. The flow rate was kept constant at 40 to 50 mL/mins. by clamping the proximal section of the shunt. The radioactivity of a 45 cm long middle section of the device also containing the short Dacron segment in a central position was measured for 5 mins. twelve times consecutively between 10 mins. and 70 mins.

At least nine consecutive experiments were performed in each study subject on separate days, with one day to several weeklong breaks between experiments. Changes in study parameters upon treatment were analyzed using the paired t-test (one or two tail) for pre-dosing versus post-dosing parameters, as well as for treatment versus control and treatment versus treatment comparisons.

Since there was no substantial thrombus formation for up to 5 minutes in the device, the first 5 minute image was used as background. Radioactivity above background in consecutive measurements indicated local deposition of radiolabeled platelets and the presence of platelet-rich thrombi. At 5 minute intervals, the number of platelets deposited on the device was calculated from radioactivities of the device and a peripheral blood sample, and the platelet count. The device was removed 70 mins. after APC or WE dosing, and the Dacron segment was saved for determination of fibrin deposition later, as described. The blood flow was restored by reconnecting the permanent AV shunt with a 5 cm long chronic access shunt segment until the next experiment. Up to three control thrombosis studies without antithrombotic treatment were also performed in each animal. Antithrombotic effect of APC or WE was defined as less platelets and/or fibrinogen deposited then in untreated controls at corresponding times.

In the shunt model, the WE variant thrombin of the present invention and high-dose APC inhibited thrombosis, defined as a decrease in the deposition of $^{111}$In-labeled platelets, when compared to corresponding controls, as shown in FIG. 7. The results as shown in FIG. 7 are displayed as the averages of measurements from three experiments for each data point following no treatment (control) or treatment with three different doses of APC or WE.

There were significantly fewer platelets deposited in all WE-treated and 0.45 mg/kg APC-treated animals than during untreated control studies (p<0.01 for each comparison from 40 mins. and 70 mins. and p<0.03 for each comparison from 10 to 70 mins). There was no demonstrable difference between the rates of platelet deposition after administration of 0.45 mg/kg of APC and WE (p>0.3 for each comparison). All administered doses of WE were more antithrombotic between 40 and 70 mins. than 0.2 mg/kg or 0.1 mg/kg of APC (p<0.03 for each). High dose APC inhibited platelet deposition by 76% at 70 mins. compared to the corresponding controls (p<0.05). Inhibition by medium and low dose APC did not reach statistical significance. The variant thrombin WE of the present invention inhibited platelet deposition by 79.5% (0.011 mg/kg) to 83% (0.055 mg/kg) at 70 mins. compared to the corresponding controls (p<0.04 for each). Increasing the dose of WE from 0.011 mg/kg to 0.055 mg/kg did not significantly increase the antithrombotic effect at any time during the 60 mins. thrombosis experiment. The highest dose of APC modestly increased template bleeding time, but all bleeding times remained under 10 mins. in each group as shown in Table 3, below.

deposition results were also evaluated using single factor analysis of variance. Regression analysis was used for establishing dose-response.

Although injection of either WE or APC resulted in profound prolongation of the APTT up to 10-fold pretreatment baseline value, no clinically obvious signs of bleeding were detected in any of the animals. Plasma protein C activity was lower than before injection of all doses of WE tested as shown in Table 3. There was a positive correlation between loss of protein C activity and the dose of WE ($R^2=0.97$). The two highest doses of WE caused partial acquired protein C deficiency, defined arbitrarily as less than 60% of baseline protein C activity. Plasma samples containing WE that were incubated for 48 hr at room temperature contained no clots. All 10 mins. and 40 mins. plasma samples from experiments with 0.11 mg/kg or 0.22 mg/kg WE doses, but not from others, contained loose plasma clots after one week incubation, consistent with the predictions from in vitro studies.

TABLE 3

Changes in platelet count, fibrinogen level, protein C level, and bleeding time to following no treatment (control) or treatment with three different doses of APC and five different doses of variant thrombin WE in baboons.

| Agent | WE | WE | WE | WE | WE | control |
|---|---|---|---|---|---|---|
| (dose in mg/Kg) | (0.22) | (0.11) | (0.055) | (0.022) | (0.011) | (0) |
| thrombus (+, yes; −, no) | − | − | + | + | + | + |
| % change in platelet count (0 vs. 70 mins)** | N/D* | N/D* | −1.6 ± 3.6 | 1.2 ± 4.2 | 3.1 ± 3.5 | −13.3 ± 1.3 |
| p*** | − | − | 0.634 | 0.902 | 0.468 | <0.001 |
| % change in fibrinogen level (0 vs. 70 mins)** | N/D* | N/D* | 3.2 ± 2.9 | −0.5 ± 2.7 | −1.8 ± 1.6 | −10.5 ± 1.3 |
| p*** | − | − | 0.382 | 0.938 | 0.316 | 0.012 |
| Change of protein C level 0 vs. 100 mins percent; mean ± SEM** | −63.1 ± 3.9 | −43.7 ± 4.5 | −23.6 ± 2.8 | −16.2 ± 1.7 | −8.1 ± 0.7 | −0.5 ± 1.8 |
| p*** | 0.014 | 0.020 | 0.029 | 0.025 | 0.002 | 0.789 |
| % change in bleeding time (0 vs. 40 mins)** | 114.7 ± 26.6 | 38.3 ± 51 | 6.6 ± 7.8 | 6.5 ± 6.8 | 19.8 ± 20.1 | −0.2 ± 7.2 |
| p*** | 0.068 | 0.099 | 0.350 | 0.666 | 0.397 | 0.807 |

| Agent | APC | APC | APC | control |
|---|---|---|---|---|
| (dose in mg/Kg) | (0.45) | (0.2) | (0.1) | (0) |
| thrombus (+, yes; −, no) | + | + | + | + |
| % change in platelet count (0 vs. 70 mins)**. | −3.3 ± 1.8 | 1.6 ± 2.6 | −6.5 ± 4.8 | −13.3 ± 1.3 |
| p*** | 0.251 | 0.481 | 0.296 | <0.001 |
| % change in fibrinogen level (0 vs. 70 mins)** | 2.7 ± 0.2 | −2.2 ± 2.7 | −5.9 ± 1.9 | −10.5 ± 1.3 |
| p*** | 0.057 | 0.507 | 0.163 | 0.012 |
| Change of protein C level 0 vs. 100 mins percent; mean ± SEM** | 2.4 ± 0.8 | 2.8 ± 0.2 | 1.5 ± 3.6 | −0.5 ± 1.8 |
| p*** | 0.072 | N/A | 0.761 | 0.789 |
| % change in bleeding time (0 vs. 40 mins)** | 55.7 ± 22.6 | 14.9 ± 13.6 | 7.7 ± 12.2 | −0.2 ± 7.2 |
| p*** | 0.047 | 0.346 | 0.707 | 0.807 |

*Not determined because these samples were not collected from the baboons.
**Given as the average of percent changes in three study subjects. Duplicate original measurements where applicable.
***Probability of difference between measured variables of "pre" and "post" parameters was determined by calculating the P value using the t-Test.

Plasma-derived and recombinant human APC have been shown to be comparably anticoagulant in plasma, and both were antithrombotic in baboons. Gruber et al. Blood 73: 639–42 (1989); Taylor et al. J. Clin. Invest. 79: 918–25 (1987). In this study, an injectable formulation of lyophilized human plasma dervied APC was used to produce antithrombotic and antihemostatic effects in the baboons. The anticoagulant activity of APC was tested prior to injection by measuring its effect on the activated partial thromboplastin time (APTT) of citrated plasma. Platelet

EXAMPLE 6

Antithrombotic Fibrin Effects of APC and Variant Thrombin WE

The systemic prothrombotic effect of the device and/or test articles were assessed indirectly by measuring clottable plasma fibrinogen levels in citrated plasma samples using the von Clauss method (thrombin clotting time of diluted plasma, averages of duplicate measurements) and whole blood platelet count in EDTA-anticoagulated blood samples (single measurements) using an automated blood analyzer. Samples were drawn before and 70 mins. after injection of the enzymes. A decrease in circulating platelet count or fibrinogen levels during experiments was considered as clinical laboratory evidence of consumption of these factors. Since WE was resistant to antithrombin, 100 μl sample aliquots of the 10 mins. and 40 mins. plasma samples were incubated for one week at room temperature to make qualitative determination of the presence or absence of weak inhibition-resistant procoagulant activity in the samples. Presence of removable fibrin clots in the test tubes indicated thrombin activity.

The amount of fibrin deposited in the Dacron graft segment after 60 mins. exposure to blood flow following no treatment (control) or treatment with three different doses of APC or WE is shown in FIG. 8. The results are shown as averages of three experiments for each column. By the end of the thrombosis experiments 70 mins. after dosing, 35.9 to 54.3% less fibrin was deposited in the thrombogenic Dacron graft segments following treatment with WE than in corresponding controls, as shown in FIG. 8. No dose-response to WE could be verified. Deposition of fibrin after APC treatment was not significantly different from corresponding controls (p>0.09 for each comparison).

EXAMPLE 7

Antihemostatic Effects of APC and WE

The antihemostatic effects of the antithrombotic enzymes were assessed following injection of 0.1, 0.2 or 0.45 mg/kg (1.8, 3.6 or 8 nmoles/kg) of APC or 0.011, 0.022, 0.055, 0.11 or 0.22 mg/kg (0.3, 0.6, 1.5, 3 or 6 nmoles/kg) of WE. Blood was drawn from the AV shunt, or by standard venepuncture in the high-dose WE studies when no thrombogenic shunt was inserted distal to the shunt. The total volume of blood drawn for all in vitro measurements was restricted to less than 10 mL per day in each study subject. Blood samples (0.45 or 0.9 mL) were drawn into 3.2% trisodium citrate at regular intervals for at least 100 mins. from time 0 (dosing) for immediate assessment of hemostasis by using point-of-care APTT testing. Samples were processed rapidly and all APTT measurements were performed between 5 and 7 mins. after blood drawing. When the APTT value was significantly prolonged, the APTT test was repeated several times on the same sample for up to 100 mins. at random intervals.

Both WE and APC treatments compromised coagulation-dependent hemostasis at all doses administered, as reflected by significant systemic anticoagulation by the time of the first blood sampling 10 mins. after dosing, as shown in FIG. 9. APTT values returned to pre-treatment baseline after APC (p>0.86 for each), but not after treatment with WE doses of 0.022 mg/kg or more (p<0.03 for each) by the end of the 100 mins. observation period. The prolongation of APTT 10 and 40 mins. after injection of WE indicated secondary anticoagulant dose response ($R^2$=0.89 and 0.93, respectively). The anticoagulant effect was disappearing from blood samples and APTT values approached those of the pre-dosing samples at comparable rates during ex vivo during incubation of citrated blood samples taken after either APC or WE treatments, as shown in Example 9, below, and FIG. 10.

Because no natural anticoagulant other than APC is known to lose its anticoagulant activity within several hours in blood, progressively decreasing APTT of a plasma sample is evidence for the presence of APC in the circulation at the time of blood drawing. As an additional safety measure, template bleeding times using pediatric devices on each study subject were also determined as described by Hanson et al. in J. Clin. Invest. 92: 2003–2012(1993) incorporated herein by reference in its entirety, at approximately 10 mins. before and 40 mins. after dosing to monitor severe compromise by APC or WE to primary hemostasis. The animals were carefully monitored for clinical signs of bleeding or disseminated intravascular coagulation. Normalization of APTT was confirmed after 24 hrs in study subjects with APTT still prolonged at 200 mins. after APC or WE dosing.

APTT values following no treatment (control) or treatment with three different doses of APC or WE are shown in FIG. 9. The results are displayed with lines connecting corresponding values of the averages of three single measurements in three experiments for each data point.

Although injection of both WE and APC resulted in up to 10-fold prolongation of the APTT compared to the pre-treatment baseline value, no clinically obvious signs of bleeding were detected in any of the animals. Plasma protein C activity was lower after than before injection of all doses of ET tested (Table 3).

EXAMPLE 8

Decay of Anticoagulant Effect of Exogenous or Endogenous APC in Plasma Samples

The decay of anticoagulant effect of exogenous or endogenous APC in plasma samples is shown in FIG. 10. The results are shown for single measurements performed consecutively at least three times in each sample with prolonged initial APTT following treatment with 0.45 mg/kg of APC (squares) or 0.055 mg/kg of WE (diamonds).

Plasma protein C activity was determined using the snake venom protein C activator, Protac, in samples drawn before and 100 mins. after WE or APC administration, essentially as described by Hanson et al. in J. Clin. Invest.; 92: 2003–2012(1993) and Martinoli & Stocker. in Thromb. Res.;43: 253–264(1986), incorporated herein by reference in their entireties; with the following modifications. All citrated baboon plasma samples saved for protein C testing were incubated at room temperature for 48 hrs prior to performing the protein C test to allow normalization of APTT in the samples. Normalization of APTT near to the 0 min. sample APTT value (within 10 secs) in samples with formerly significantly prolonged APTT was confirmed prior to protein C testing in each case. Pooled normal baboon plasma, also incubated for 48 hrs was diluted 1:1 in protein C depleted human plasma, and then in serial dilutions, to generate a protein C activity standard curve.

The baboon samples were diluted 1:3 with protein C-depleted human plasma. Lyophilized Protac C vials were reconstituted into 3 mL volume as recommended by the manufacturers (American Diagnostica, Greenwich, Conn.), and 40 μl of the activator was incubated with 20 μl of the 1:3 diluted baboon sample at 37 C for 1 min. before adding a 30 μl aliquot of the mixture to the APTT card. Protein C activity of the samples was determined in percentage using the standard curve generated using pooled baboon plasma.

The results are shown in FIG. 10 for single measurements performed consecutively at least three times in each sample with prolonged initial APTT following treatment with 0.45 mg/kg of APC (squares) or 0.055 mg/kg of WE (diamonds).

EXAMPLE 9

Figure 11:
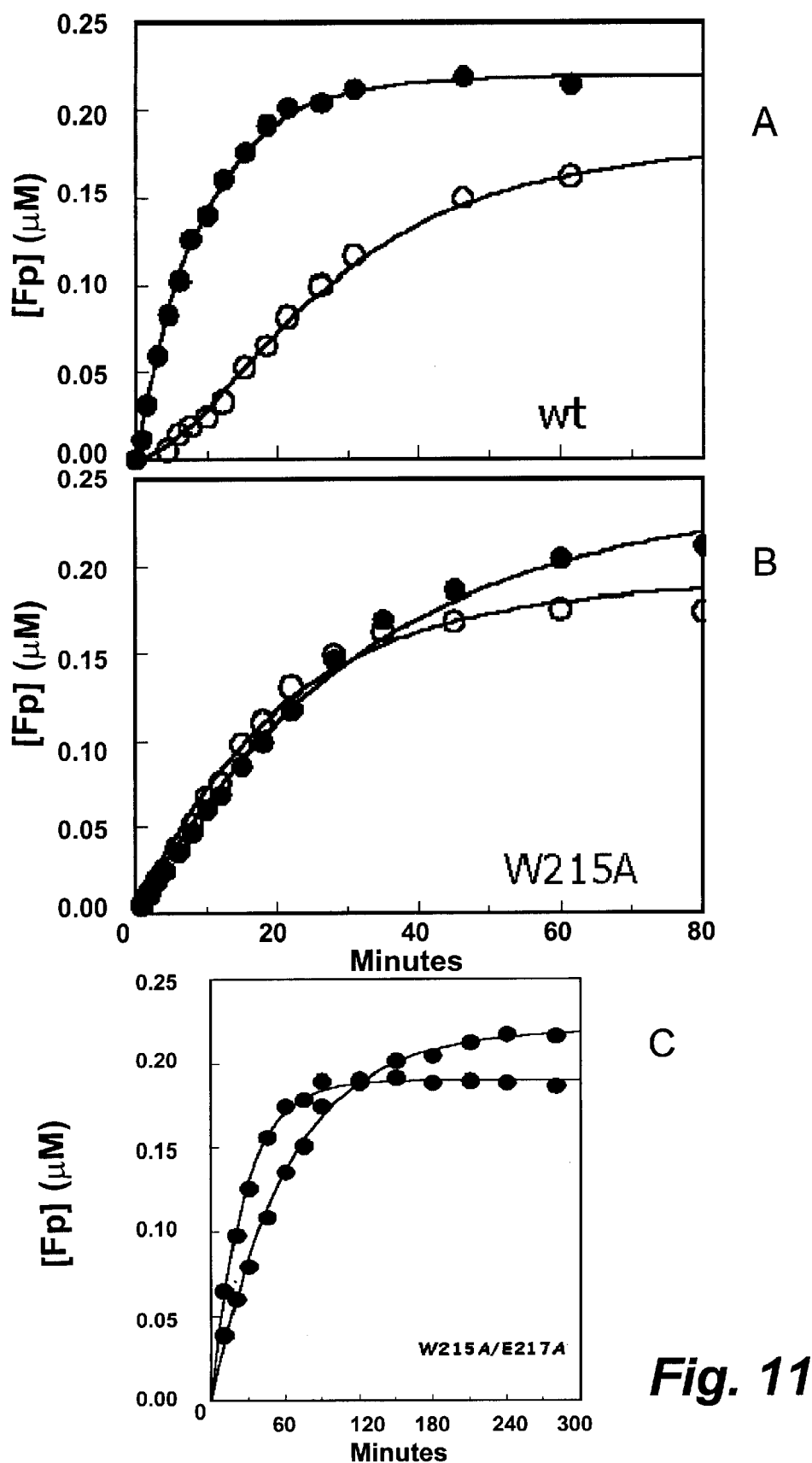

Release of Fibrinopeptides A and B by Wild-type and W215A/E217A Variants of Thrombin Progress curves of the release of fibrinopeptides A (●) and B (○) by wild-type and the WE W215A/E217A mutant of thrombin are shown in FIG. 11. Continuous lines were drawn using eqs 3a and 3b of Vindigni and Di Cera Biochemistry 35 4417–4426 (1996), with $\kappa_1$ and $\kappa_2$ expressed as the value of $s=k_{cat}/K_m$ for the release of fibrinopeptide, $s_1$ for fibrinopeptide A (FpA) and $s_2$ for fibrinopeptide B (FpB), times the concentration of thrombin $e_T$. The best-fit parameter values are: wt, $[FpA]_\infty=0.22\pm0.01$ $\mu M$, $s_1=17\pm1\,\mu M^{-2}\,s^{-1}$, $f[FpB]_\infty=0.18\pm0.01\,\mu M$, $s_2=8.1\pm0.5$ $\mu M^{-1}s^{-1}$, $e_T=0.1$ nM; W215A/E217A, $[FpA]_\infty=0.22\pm0.01$ $\mu M$, $s_1=0.00089\pm0.00007\,\mu M^{-1}s^{-1}$, $f[FpB]_\infty=0.19\pm0.01\,\mu M$, $s_2=0.0021\pm0.0001$ mM$^{-1}s^{-1}$, $e_T=300$ nM (see also Table 1). In the case of WE, the parameters for the release of fibrinopeptide B refer to an equation of the same form as eq 3a of Vindigni & Di Cera because no lag phase was observed. Experimental conditions are: 5 mM Tris, 0.1% PEG, 145 mM NaCl, pH 7.4, 37° C. The release of fibrinopeptides by the WE variant is approximately 7-fold slower compared to wild-type, although the enzyme concentration used in the assay is 3,000-fold higher.

EXAMPLE 10

Activation of Protein C by Wild-type and W215A/E217A (WE) Variants of Thrombin Progress curves of the activation of protein C by wild-type (●) and the W215A/E217A mutant (○) of thrombin, in the presence of thrombomodulin are shown in FIG. 12. The data depict the absorbance change at 405 nm due to the release of p-nitroaniline from the chromogenic substrate H-D-Asp-Arg-Arg-p-nitroanilide by activated protein C, after activation by thrombin. Continuous lines were drawn from integrated rate equations using the values of $k_{cat}/K_m$ for the hydrolysis of protein C reported in Table 3. Experimental conditions are: 5 mM Tris, 0.1% PEG, 145 mM NaCl, 5 mM CaCl$_2$, 100 nM rabbit thrombomodulin, 400 nM protein C, 50 $\mu$M DRR, pH 7.4, 37° C. The concentration of thrombin wild-type or W215A/E217A mutant is 0.2 nM. The curve relative to the activation of protein C by the mutant W215A/E217A is only 7-fold slower compared to wild-type, although the enzyme concentration is the same, as opposed to the effect shown in FIG. 1 of Example 9 above, for the cleavage of fibrinogen.

EXAMPLE 11

In vitro Activation of Protein C

Plasma protein C activity was determined using a snake venom protein C activator in samples drawn before and 100 minutes after WE or APC administration, essentially as described in Hanson et al. J. Clin. Invest. 92: 2003–2012 (1993) and Martinoli & Tocker. Thromb. Res. 43: 253–264 (1986) incorporated herein by reference in their entireties and with the following modifications. All citrated baboon plasma samples saved for protein C testing were incubated at room temperature for 48 hours prior to performing the protein C test to allow normalization of APTT in the samples. Normalization of APTT near to the 0 min. sample APTT value (within 10 seconds) in samples with formerly significantly prolonged APTT was confirmed prior to protein C testing in each case. Pooled normal baboon plasma, also incubated for 48 hours was diluted 1:1 in protein C depleted human plasma (George King Bio-Medical, Overland Park, Kans.), and then in serial dilutions, to generate a protein C activity standard curve. The baboon samples were diluted 1:3 with protein C-depleted human plasma. Lyophilized Protac C vials were reconstituted into 3 mL volume as recommended (American Diagnostica, Greenwich, Conn.), and 40 $\mu$l of the activator was incubated with 20 pi of the 1:3 diluted baboon sample at 37° C. for 1 min. before adding a 30 $\mu$l aliquot of the mixture to the APTT card. Protein C activity of the samples was determined in percentage using the standard curve generated using pooled baboon plasma.

EXAMPLE 12

Anticoagulant Activities of APC and the WT and WE Variant Thrombin

APC was a potent anticoagulant that prolonged with similar efficiency the APTT of both baboon and human plasma, as shown in FIG. 13A. WE was a weak procoagulant because it clotted baboon plasma. However, WT was a more than 500-fold more potent procoagulant than WE in the tested concentration range, as shown in FIG. 13B. Assuming 60 mL blood volume per kg body weight in the baboons, the theoretical peak blood concentration of APC (78.8 nM) after its highest dose (0.45 mg/kg), in vivo, was above the high end of the anticoagulant range tested, in vitro. The theoretical peak blood concentration of WE (39.8 nM) after its highest dose (0.22 mg/kg), in vivo, was two orders of magnitude below its detectably procoagulant concentration, in vitro. Plasma samples that were incubated for 48 hours at room temperature contained no clots. However, all 10 mins. and 40 mins. plasma samples from experiments with 0.11 mg/kg or 0.22 mg/kg WE doses but not from others contained loose plasma clots after one week incubation, indicating the presence of free trace procoagulant thrombin activity.

What is claimed is:

1. A variant thrombin comprising an amino acid sequence having the substitutions W215A and E217A wherein the amino acid sequence is at least 80% identical to the sequence set forth in SEQ ID NO: 3 and wherein the variant has protein C-activating activity and reduced platelet activating and fibrinogen cleavage activities compared to the parental thrombin.

2. The variant thrombin according to claim 1 comprising a thrombin B-chain comprising the amino acid sequence as set forth in SEQ ID NO: 4.

3. The variant thrombin according to claim 1, wherein the variant thrombin is encoded by a nucleic acid comprising the sequence as set forth in SEQ ID NO: 5, or a degenerate variant thereof.

4. The variant thrombin according to claim 2, wherein the variant thrombin is encoded by a nucleic acid comprising the sequence as set forth in SEQ ID NO: 6, or a degenerate variant thereof.

5. The variant thrombin according to claim 1 having a ratio of the percent of wild-type protein C activation (PA) activity in a thrombin variant relative to the percent of wild-type fibrinogen clotting (FC) activity in the variant (PA/FC ratio) greater than 1.

6. The variant thrombin according to claim 1 having a ratio of the percent of wild-type protein C activation (PA) activity in a thrombin variant relative to the percent of wild-type fibrinogen clotting (FC) activity in the variant (PA/FC ratio) greater than 150.

7. The variant thrombin according to claim 1, wherein the variant thrombin is expressed from a recombinant nucleic acid within a cell.

8. The variant thrombin according to claim 7, wherein the recombinant nucleic acid comprises a sequence selected from SEQ ID NO: 5 and SEQ ID NO: 6, or a degenerate variant thereof.

9. A physiologically acceptable composition comprising:

(a) a variant thrombin comprising an amino acid sequence having the substitutions W215A and E217A wherein the amino acid sequence is at least 80% identical to the sequence set forth in SEQ ID NO: 3 and wherein the variant has protein C-activating activity and reduced platelet activating and fibrinogen cleavage activities compared to the parental thrombin; and (b) at least one pharmaceutically acceptable carrier.

10. The physiologically acceptable composition according to claim 9, wherein the variant thrombin has the amino acid substitutions W215A and E217A, and comprises the amino acid sequence set forth in SEQ ID NO: 3.

11. The physiologically acceptable composition according to claim 9, wherein the variant thrombin has the amino acid substitutions W215A and E217A, and comprises the amino acid sequence set forth in SEQ ID NO: 4.

12. A kit comprising a variant thrombin with reduced procoagulant and platelet activating activity and comprising an amino acid sequence selected from SEQ ID NOS: 3 and 4, and packaging comprising instructions for using the variant thrombin as an antithrombotic agent in a recipient animal or human.

13. The kit according to claim 12, further comprising a pharmaceutically acceptable carrier and instructions for use in delivering the variant thrombin to an animal or human.

14. A kit comprising a variant thrombin with reduced procoagulant activity and comprising the amino acid sequence selected from SEQ ID NOS: 3 and 4, and packaging comprising instructions for using the variant thrombin to determine the endogenous antithrombotic potential of the protein C system of an animal or human.

* * * * *

UNITED STATES PATENT AND TRADEMARK OFFICE
CERTIFICATE OF CORRECTION

PATENT NO. : 6,706,512 B2
DATED : March 16, 2004
INVENTOR(S) : Gruber et al.

It is certified that error appears in the above-identified patent and that said Letters Patent is hereby corrected as shown below:

<u>Title page,</u>
Item [75], Replace "De Cera" with -- Di Cera --.

Signed and Sealed this

Twenty-ninth Day of June, 2004

JON W. DUDAS
*Acting Director of the United States Patent and Trademark Office*

SEQUENCE LISTING

```
<160> NUMBER OF SEQ ID NOS: 13

<210> SEQ ID NO 1
<211> LENGTH: 295
<212> TYPE: PRT
<213> ORGANISM: Homo sapiens
<220> FEATURE:
<221> NAME/KEY: CHAIN
<222> LOCATION: (1)..(36)
<223> OTHER INFORMATION: Thrombin W215A  A-Chain
<220> FEATURE:
<221> NAME/KEY: CHAIN
<222> LOCATION: (37)..(295)
<223> OTHER INFORMATION: Thrombin W215A  B-Chain

<400> SEQUENCE: 1

Thr Phe Gly Ser Gly Glu Ala Asp Cys Gly Leu Arg Pro Leu Phe Glu
1               5                   10                  15
```

-continued

Lys Lys Ser Leu Glu Asp Lys Thr Glu Arg Glu Leu Leu Glu Ser Tyr
            20                  25                  30

Ile Asp Gly Arg Ile Val Glu Gly Ser Asp Ala Glu Ile Gly Met Ser
            35                  40                  45

Pro Trp Gln Val Met Leu Phe Arg Lys Ser Pro Gln Glu Leu Leu Cys
    50                  55                  60

Gly Ala Ser Leu Ile Ser Asp Arg Trp Val Leu Thr Ala Ala His Cys
65                  70                  75                  80

Leu Leu Tyr Pro Pro Trp Asp Lys Asn Phe Thr Glu Asn Asp Leu Leu
                85                  90                  95

Val Arg Ile Gly Lys His Ser Arg Thr Arg Tyr Glu Arg Asn Ile Glu
            100                 105                 110

Lys Ile Ser Met Leu Glu Lys Ile Tyr Ile His Pro Arg Tyr Asn Trp
            115                 120                 125

Arg Glu Asn Leu Asp Arg Asp Ile Ala Leu Met Lys Leu Lys Lys Pro
            130                 135                 140

Val Ala Phe Ser Asp Tyr Ile His Pro Val Cys Leu Pro Asp Arg Glu
145                 150                 155                 160

Thr Ala Ala Ser Leu Leu Gln Ala Gly Tyr Lys Gly Arg Val Thr Gly
                165                 170                 175

Trp Gly Asn Leu Lys Glu Thr Trp Thr Ala Asn Val Gly Lys Gly Gln
            180                 185                 190

Pro Ser Val Leu Gln Val Val Asn Leu Pro Ile Val Glu Arg Pro Val
            195                 200                 205

Cys Lys Asp Ser Thr Arg Ile Arg Ile Thr Asp Asn Met Phe Cys Ala
    210                 215                 220

Gly Tyr Lys Pro Asp Glu Gly Lys Arg Gly Asp Ala Cys Glu Gly Asp
225                 230                 235                 240

Ser Gly Gly Pro Phe Val Met Lys Ser Pro Phe Asn Asn Arg Trp Tyr
                245                 250                 255

Gln Met Gly Ile Val Ser Ala Gly Glu Gly Cys Asp Arg Asp Gly Lys
            260                 265                 270

Tyr Gly Phe Tyr Thr His Val Phe Arg Leu Lys Lys Trp Ile Gln Lys
            275                 280                 285

Val Ile Asp Gln Phe Gly Glu
    290                 295

<210> SEQ ID NO 2
<211> LENGTH: 259
<212> TYPE: PRT
<213> ORGANISM: Homo sapiens
<220> FEATURE:
<221> NAME/KEY: CHAIN
<222> LOCATION: (1)..(259)
<223> OTHER INFORMATION: Thrombin W215A B-Chain

<400> SEQUENCE: 2

Ile Val Glu Gly Ser Asp Ala Glu Ile Gly Met Ser Pro Trp Gln Val
1               5                   10                  15

Met Leu Phe Arg Lys Ser Pro Gln Glu Leu Leu Cys Gly Ala Ser Leu
            20                  25                  30

Ile Ser Asp Arg Trp Val Leu Thr Ala Ala His Cys Leu Leu Tyr Pro
            35                  40                  45

Pro Trp Asp Lys Asn Phe Thr Glu Asn Asp Leu Leu Val Arg Ile Gly
        50                  55                  60

-continued

```
Lys His Ser Arg Thr Arg Tyr Glu Arg Asn Ile Glu Lys Ile Ser Met
 65                  70                  75                  80

Leu Glu Lys Ile Tyr Ile His Pro Arg Tyr Asn Trp Arg Glu Asn Leu
                 85                  90                  95

Asp Arg Asp Ile Ala Leu Met Lys Leu Lys Pro Val Ala Phe Ser
            100                 105                 110

Asp Tyr Ile His Pro Val Cys Leu Pro Asp Arg Glu Thr Ala Ala Ser
            115                 120                 125

Leu Leu Gln Ala Gly Tyr Lys Gly Arg Val Thr Gly Trp Gly Asn Leu
    130                 135                 140

Lys Glu Thr Trp Thr Ala Asn Val Gly Lys Gly Gln Pro Ser Val Leu
145                 150                 155                 160

Gln Val Val Asn Leu Pro Ile Val Glu Arg Pro Val Cys Lys Asp Ser
                165                 170                 175

Thr Arg Ile Arg Ile Thr Asp Asn Met Phe Cys Ala Gly Tyr Lys Pro
            180                 185                 190

Asp Glu Gly Lys Arg Gly Asp Ala Cys Glu Gly Asp Ser Gly Gly Pro
            195                 200                 205

Phe Val Met Lys Ser Pro Phe Asn Asn Arg Trp Tyr Gln Met Gly Ile
    210                 215                 220

Val Ser Ala Gly Glu Gly Cys Asp Arg Asp Gly Lys Tyr Gly Phe Tyr
225                 230                 235                 240

Thr His Val Phe Arg Leu Lys Lys Trp Ile Gln Lys Val Ile Asp Gln
                245                 250                 255

Phe Gly Glu

<210> SEQ ID NO 3
<211> LENGTH: 295
<212> TYPE: PRT
<213> ORGANISM: Homo sapiens
<220> FEATURE:
<221> NAME/KEY: CHAIN
<222> LOCATION: (1)..(36)
<223> OTHER INFORMATION: Thrombin WE A-Chain
<220> FEATURE:
<221> NAME/KEY: CHAIN
<222> LOCATION: (37)..(295)
<223> OTHER INFORMATION: Thrombin WE B-Chain

<400> SEQUENCE: 3

Thr Phe Gly Ser Gly Glu Ala Asp Cys Gly Leu Arg Pro Leu Phe Glu
  1               5                  10                  15

Lys Lys Ser Leu Glu Asp Lys Thr Glu Arg Glu Leu Leu Glu Ser Tyr
                 20                  25                  30

Ile Asp Gly Arg Ile Val Glu Gly Ser Asp Ala Glu Ile Gly Met Ser
            35                  40                  45

Pro Trp Gln Val Met Leu Phe Arg Lys Ser Pro Gln Glu Leu Leu Cys
    50                  55                  60

Gly Ala Ser Leu Ile Ser Asp Arg Trp Val Leu Thr Ala Ala His Cys
 65                  70                  75                  80

Leu Leu Tyr Pro Pro Trp Asp Lys Asn Phe Thr Glu Asn Asp Leu Leu
                 85                  90                  95

Val Arg Ile Gly Lys His Ser Arg Thr Arg Tyr Glu Arg Asn Ile Glu
            100                 105                 110

Lys Ile Ser Met Leu Glu Lys Ile Tyr Ile His Pro Arg Tyr Asn Trp
            115                 120                 125

Arg Glu Asn Leu Asp Arg Asp Ile Ala Leu Met Lys Leu Lys Lys Pro
```

```
            130                 135                 140
Val Ala Phe Ser Asp Tyr Ile His Pro Val Cys Leu Pro Asp Arg Glu
145                 150                 155                 160

Thr Ala Ala Ser Leu Leu Gln Ala Gly Tyr Lys Gly Arg Val Thr Gly
                165                 170                 175

Trp Gly Asn Leu Lys Glu Thr Trp Thr Ala Asn Val Gly Lys Gly Gln
                180                 185                 190

Pro Ser Val Leu Gln Val Val Asn Leu Pro Ile Val Glu Arg Pro Val
                195                 200                 205

Cys Lys Asp Ser Thr Arg Ile Arg Ile Thr Asp Asn Met Phe Cys Ala
                210                 215                 220

Gly Tyr Lys Pro Asp Glu Gly Lys Arg Gly Asp Ala Cys Glu Gly Asp
225                 230                 235                 240

Ser Gly Gly Pro Phe Val Met Lys Ser Pro Phe Asn Asn Arg Trp Tyr
                245                 250                 255

Gln Met Gly Ile Val Ser Ala Gly Ala Gly Cys Asp Arg Asp Gly Lys
                260                 265                 270

Tyr Gly Phe Tyr Thr His Val Phe Arg Leu Lys Lys Trp Ile Gln Lys
                275                 280                 285

Val Ile Asp Gln Phe Gly Glu
                290                 295

<210> SEQ ID NO 4
<211> LENGTH: 259
<212> TYPE: PRT
<213> ORGANISM: Homo sapiens
<220> FEATURE:
<221> NAME/KEY: CHAIN
<222> LOCATION: (1)..(259)
<223> OTHER INFORMATION: Thrombin WE B-Chain

<400> SEQUENCE: 4

Ile Val Glu Gly Ser Asp Ala Glu Ile Gly Met Ser Pro Trp Gln Val
1               5                   10                  15

Met Leu Phe Arg Lys Ser Pro Gln Glu Leu Leu Cys Gly Ala Ser Leu
                20                  25                  30

Ile Ser Asp Arg Trp Val Leu Thr Ala Ala His Cys Leu Leu Tyr Pro
                35                  40                  45

Pro Trp Asp Lys Asn Phe Thr Glu Asn Asp Leu Leu Val Arg Ile Gly
                50                  55                  60

Lys His Ser Arg Thr Arg Tyr Glu Arg Asn Ile Glu Lys Ile Ser Met
65                  70                  75                  80

Leu Glu Lys Ile Tyr Ile His Pro Arg Tyr Asn Trp Arg Glu Asn Leu
                85                  90                  95

Asp Arg Asp Ile Ala Leu Met Lys Leu Lys Lys Pro Val Ala Phe Ser
                100                 105                 110

Asp Tyr Ile His Pro Val Cys Leu Pro Asp Arg Glu Thr Ala Ala Ser
                115                 120                 125

Leu Leu Gln Ala Gly Tyr Lys Gly Arg Val Thr Gly Trp Gly Asn Leu
                130                 135                 140

Lys Glu Thr Trp Thr Ala Asn Val Gly Lys Gly Gln Pro Ser Val Leu
145                 150                 155                 160

Gln Val Val Asn Leu Pro Ile Val Glu Arg Pro Val Cys Lys Asp Ser
                165                 170                 175

Thr Arg Ile Arg Ile Thr Asp Asn Met Phe Cys Ala Gly Tyr Lys Pro
                180                 185                 190
```

```
Asp Glu Gly Lys Arg Gly Asp Ala Cys Glu Gly Asp Ser Gly Gly Pro
            195                 200                 205

Phe Val Met Lys Ser Pro Phe Asn Asn Arg Trp Tyr Gln Met Gly Ile
        210                 215                 220

Val Ser Ala Gly Ala Gly Cys Asp Arg Asp Gly Lys Tyr Gly Phe Tyr
225                 230                 235                 240

Thr His Val Phe Arg Leu Lys Lys Trp Ile Gln Lys Val Ile Asp Gln
                245                 250                 255

Phe Gly Glu

<210> SEQ ID NO 5
<211> LENGTH: 888
<212> TYPE: DNA
<213> ORGANISM: Homo sapiens
<220> FEATURE:
<221> NAME/KEY: misc_feature
<222> LOCATION: (1)..(108)
<223> OTHER INFORMATION: Coding thrombin WE A-Chain
<220> FEATURE:
<221> NAME/KEY: misc_feature
<222> LOCATION: (109)..(888)
<223> OTHER INFORMATION: Coding thrombin WE B-Chain

<400> SEQUENCE: 5
acctttggct cgggagaggc agactgtggg ctgcgacctc tgttcgagaa gaagtcgctg      60
gaggacaaaa ccgaaagaga gctcctggaa tcctacatcg acgggcgcat tgtggagggc    120
tcggatgcag agatcggcat gtcaccttgg caggtgatgc ttttccggaa gagtccccag    180
gagctgctgt gtggggccag cctcatcagt gaccgctggg tcctcaccgc cgcccactgc    240
ctcctgtacc cgccctggga caagaacttc accgagaatg accttctggt gcgcattggc    300
aagcactccc gcaccaggta cgagcgaaac attgaaaaga tatccatgtt ggaaaagatc    360
tacatccacc ccaggtacaa ctggcgggag aacctggacc gggacattgc cctgatgaag    420
ctgaagaagc tgttgccctt cagtgactac attcacctg tgtgtctgcc cgacagggag     480
acggcagcca gcttgctcca ggctggatac aaggggcggg tgacaggctg gggcaacctg    540
aaggagacgt ggacagccaa cgttggtaag gggcagccca gtgtcctgca ggtggtgaac    600
ctgcccattg tggagcggcc ggtctgcaag gactccaccc ggatccgcat cactgacaac    660
atgttctgtg ctggttacaa gcctgatgaa gggaaacgag gggatgcctg tgaaggtgac    720
agtgggggac cctttgtcat gaagagcccc tttaacaacc gctggtatca aatgggcatc    780
gtctcagcgg gtgcaggctg tgaccgggat gggaaatatg gcttctacac acatgtgttc    840
cgcctgaaga gtggataca gaaggtcatt gatcagtttg gagagtag                  888

<210> SEQ ID NO 6
<211> LENGTH: 780
<212> TYPE: DNA
<213> ORGANISM: Homo sapiens
<220> FEATURE:
<221> NAME/KEY: misc_feature
<222> LOCATION: (1)..(780)
<223> OTHER INFORMATION: Coding thrombin WE B-Chain

<400> SEQUENCE: 6
attgtggagg gctcggatgc agagatcggc atgtcacctt ggcaggtgat gcttttccgg     60
aagagtcccc aggagctgct gtgtggggcc agcctcatca gtgaccgctg ggtcctcacc    120
gccgcccact gcctcctgta cccgccctgg gacaagaact tcaccgagaa tgaccttctg    180
```

```
gtgcgcattg gcaagcactc ccgcaccagg tacgagcgaa acattgaaaa gatatccatg      240
ttggaaaaga tctacatcca ccccaggtac aactggcggg agaacctgga ccgggacatt      300
gccctgatga agctgaagaa gcctgttgcc ttcagtgact acattcaccc tgtgtgtctg      360
cccgacaggg agacggcagc cagcttgctc caggctggat acaaggggcg ggtgacaggc      420
tggggcaacc tgaaggagac gtggacagcc aacgttggta aggggcagcc cagtgtcctg      480
caggtggtga acctgcccat tgtggagcgg ccggtctgca aggactccac ccggatccgc      540
atcactgaca acatgttctg tgctggttac aagcctgatg aagggaaacg aggggatgcc      600
tgtgaaggtg acagtggggg acccttgtc atgaagagcc cctttaacaa ccgctggtat       660
caaatgggca tcgtctcagc gggtgcaggc tgtgaccggg atgggaaata tggcttctac      720
acacatgtgt tccgcctgaa gaagtggata cagaaggtca ttgatcagtt tggagagtag      780
```

<210> SEQ ID NO 7
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(16)
<223> OTHER INFORMATION: Misc_feature

<400> SEQUENCE: 7
gggcatcgtc tcannnggtg aaggctgtg                                        29

<210> SEQ ID NO 8
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(16)
<223> OTHER INFORMATION: Misc_feature

<400> SEQUENCE: 8
cacagccttc accnnntgag acgatgccc                                        29

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
gaagatctac atccaccccca gg                                              22

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
tgaccatgat tacgaattc                                                   19

<210> SEQ ID NO 11
<211> LENGTH: 35

```
<212> TYPE: DNA
<213> ORGANISM: Artificial Sequence
<220> FEATURE:
<223> OTHER INFORMATION: Primer

<400> SEQUENCE: 11
gggcatcgtc tcagcgggtg caggctgtga ccggg                                35

<210> SEQ ID NO 12
<211> LENGTH: 35
<212> TYPE: DNA
<213> ORGANISM: Artificial Sequence
<220> FEATURE:
<223> OTHER INFORMATION: Primer

<400> SEQUENCE: 12
cccggtcaca gcctgcaccc gctgagacga tgccc                                35

<210> SEQ ID NO 13
<211> LENGTH: 30
<212> TYPE: PRT
<213> ORGANISM: Artificial Sequence
<220> FEATURE:
<223> OTHER INFORMATION: TR33-62

<400> SEQUENCE: 13

Ala Thr Asn Ala Thr Leu Asp Pro Arg Ser Phe Leu Leu Arg Asn Pro
 1               5                  10                  15

Asn Asp Lys Tyr Glu Pro Phe Trp Glu Asp Glu Glu Lys Asn
                20                  25                  30
```